(12) United States Patent
Zhang et al.

(10) Patent No.: US 7,288,407 B2
(45) Date of Patent: Oct. 30, 2007

(54) STABLE CYTOCHROME P450 24 (CYP24) EXPRESSING CELL LINE AND METHODS AND USES THEREOF

(75) Inventors: Anqi Zhang, Westborough, MA (US); Mian Gao, North York (CA)

(73) Assignee: Cytochroma, Inc., Ontario (CA)

( * ) Notice: Subject to any disclaimer, the term of this patent is extended or adjusted under 35 U.S.C. 154(b) by 0 days.

(21) Appl. No.: 10/513,302

(22) PCT Filed: May 2, 2003

(86) PCT No.: PCT/CA03/00620

§ 371 (c)(1),
(2), (4) Date: Oct. 3, 2005

(87) PCT Pub. No.: WO03/093459

PCT Pub. Date: Nov. 13, 2003

(65) Prior Publication Data

US 2006/0105417 A1 May 18, 2006

Related U.S. Application Data

(60) Provisional application No. 60/376,806, filed on May 2, 2002.

(51) Int. Cl.
*C07H 21/04* (2006.01)
*C12Q 1/26* (2006.01)
*C12N 9/02* (2006.01)

(52) U.S. Cl. ............... 435/325; 435/25; 435/69.1; 435/189; 435/320.1; 536/23.2

(58) Field of Classification Search ............ 435/25, 435/189, 320, 69.1; 536/23.2
See application file for complete search history.

(56) References Cited

U.S. PATENT DOCUMENTS

| | | | |
|---|---|---|---|
| 4,373,071 A | 2/1983 | Itakura | |
| 4,401,796 A | 8/1983 | Itakura | |
| 4,458,066 A | 7/1984 | Caruthers et al. | |
| 4,598,049 A | 7/1986 | Zelinka et al. | |
| 2005/0042730 A1 * | 2/2005 | Kato et al. .............. | 435/69.1 |

FOREIGN PATENT DOCUMENTS

| WO | WO 97/49815 A1 | 12/1997 |
|---|---|---|
| WO | WO 01/44443 A2 | 6/2001 |

OTHER PUBLICATIONS

Sakaki et al. J. Biosci. Bioengin 2000, vol. 90, pp. 583-590.*
Chen et al . PNAS 1993, 90, 4543-4547.*
Beal et al., "Second Structural Motif for Recognition of DNA by Oligonucleotide-Directed Triple-Helix Formation", Science, Mar. 15, 1991, vol. 251(4999), pp. 1360-1363.
Bligh et al., Can. J. Biochem.37:911-917. 1959.
Brutlag et al., "Improved sensitivity of biological sequence database searches", Comput Appl Biosci., vol. 6(3), pp. 237-245, USA.
Chen et al., "Isolation and expression of human 1,-25-dihydroxyvitamin D3 24-hydroxylase cDNA" Proc. Natl. Acad. Sci. USA, May 15, 1993, vol. 90(10), pp. 4543-4547, U.S.A.
Cooney et al., "Site-Specific Oligonucleotide Binding Represses Transcription of the Human c-*myc* Gene in Vitro", Science, Jul. 22, 1988, vol. 241(4864), pp. 456-459.
Dilworth et al., "Different Mechanisms of Hydroxylation Site Selection by Liver and Kidney Cytochrome P450 Species (CYP27 adn CYP24) Involved in Vitamin D Metabolism", J. Biol. Chem., Jul. 14, 1995, vol. 270(28), pp. 16766-16774, U.S.A.
Itoh et al., "Molecular cloning of 25-hydroxyvitamin D-3 24-hydroxylase (Cyp-24) from mouse kidney: its inducibility by vitamin D-3", Biochim. Biophys. Acta., Oct. 17, 1995, vol. 1264(1), pp. 26-28.
Itoh et al., "Simultaneous expression of ferredoxin, ferredoxin reductase and P450 in COS7 cells", Biochim. Biophys. Acta., Jan. 16, 1997, vol. 1318(1-2), pp. 284-290.
Jones et al., "Expression and Activity of Vitamin D-Metabolizing Cytochrome P450s (CYP1α and CYP24) in Human Nonsmall Cell Lung Carcinomas", Endocrinology, Jul. 1999, vol. 140(7), pp. 3303-3310.
Kaufman et al., Poster Presentation: 23rd Annual Meeting of the American Society for Bone and Mineral Research, J. Bone Miner. Res., Oct. 12-16, 2001, vol. 16(Supp. 1), Abstract SA529, U.S.A.
Lee et al., "Complexes formed by (pyrimidine)$_n$ (purine)$_n$ DNAs on lowering the pH are three-sided", Nucl. Acids Res., Apr. 2, 1979, vol. 6(9), pp. 3073-3091.
Masuda et al., "Vitamin D Analogs- Drug Design Based on Proteins Involved in Vitamin D Signal Transduction", Curr. Drug Targets Immune Endocr Metabol Disord, Mar. 2003, vol. 3(1), pp. 43-66.
Peehl et al., "Preclinical Activity of Ketoconazole in Combination With Calcitriol or the Vitamin D Analogue Eb 1089 in Prostate Cancer Cells", J Urol, Oct. 2002, vol. 168(4, pt. 1of2), pp. 1583-1588.
Okano, "Oligodeoxynucleotides as Antisense Inhibitors of Gene Expression", J. Neurochem, 1991, vol. 56(560).
Ray et al., "Metabolism of 2 3H-1alpha, 2-dihydroxyvitamin D3 in the cultures human keratinocytes" J. Cell. Biochem., 1995, vol. 59(1), pp. 117-122.
Schuster et al., "Selective inhibition if vitamin D hydroxylases in human keratinocytes", Steroids, May 1, 2001, vol. 66(5), pp. 409-422.
Sakaki et al., "Dual metabolic pathway of 25-hydroxyvitamin $D_3$ catalyzed by human CYP24", Eur. J. Biochem., Oct. 2000, vol. 267(20), pp. 6158-6165.
White et al., "Identification of the Retinoic Acid-inducible All-trans-retinoic Acid 4-Hydroxylase", J. Biol. Chem., Nov. 22, 1996, vol. 271(47), pp. 29922-29927, U.S.A.

\* cited by examiner

*Primary Examiner*—Ponnathapu Achutamurthy
*Assistant Examiner*—Mohammad Y. Meah
(74) *Attorney, Agent, or Firm*—Marshall, Gerstein & Borun LLP

(57) ABSTRACT

The invention relates to a stable recombinant host cell comprising a CYP24 nucleic acid. The host cell is preferably a mammalian cell or an insect cell. The cell is useful for identifying modulators of CYP24 that can be used in the treatment of CYP24 expression-related medical conditions.

10 Claims, 12 Drawing Sheets

\* P: positive control; N: negative control

Lane 1: CYP24H6
Lane 2: CYP24 with adrenodoxin (ADX)
Lane 3: CYP24 with adrenodoxin reductase (ADR)
Lane 4: CYP24 with both ADX and ADR

```
GCTAGCACCATGAGCTCCCCCATCAGCAAGAGCCGCTCGCTTGCCGCCTTCCTGCAGCAGCTGCGCAGTCC
GAGGCAGCCCCCGAGACTGGTGACATCTACGGCGTACACGTCCCCTCAGCCGCGAGAGGTGCCAGTCTGCC
CGCTGACAGCTGGTGGCGAGACTCAGAACGCGGCCGCCCTGCCGGGCCCCACCAGCTGGCCACTGCTGGGC
AGCCTGCTGCAGATTCTCTGGAAAGGGGGTCTCAAGAAACAGCACGACACCCTGGTGGAGTACCACAAGAA
GTATGGCAAGATTTTCCGCATGAAGTTGGGTTCCTTTGAGTCGGTGCACCTGGGCTCGCCATGCCTGCTGG
AAGCGCTGTACCGCACCGAGAGCGCGTACCCGCAGCGGCTGGAGATCAAACCGTGGAAGGCCTATCGCGAC
TACCGCAAAGAAGGCTACGGGCTGCTGATCCTGGAAGGGGAAGACTGGCAGCGGGTCCGGAGTGCCTTTCA
AAAGAAACTAATGAAACCAGGGGAAGTGATGAAGCTGGACAACAAAATCAATGAGGTCTTGGCCGATTTTA
TGGGCAGAATAGATGAGCTCTGTGATGAAAGAGGCCACGTTGAAGACTTGTACAGCGAACTGAACAAATGG
TCGTTTGAAAGTATCTGCCTCGTGTTGTATGAAGAGATTTGGGCTTCTCCAGAAGAATGCAGGGGATGA
AGCTGTGAACTTCATCATGGCCATCAAAACAATGATGAGCACGTTTGGGAGGATGATGGTCACTCCAGTCG
AGCTGCACAAGAGCCTCAACACCAAGGTCTGGCAGGACCACACTCTGGCCTGGGACACCATTTTCAAATCA
GTCAAAGCTTGTATCGACAACCGGTTAGAGAAGTATTCTCAGCAGCCTAGTGCAGATTTCCTTTGTGACAT
TTATCACCAGAATCGGCTTTCAAAGAAAGAATTGTATGCTGCTGTCACAGAGCTCCAGCTGGCTGCGGTGG
AAACGACAGCAAACAGTCTAATGTGGATTCTCTACAATTTATCCCGTAATCCCCAAGTGCAACAAAAGCTT
CTTAAGGAAATTCAAAGTGTATTACCTGAGAATCAGGTGCCACGGGCAGAAGATTTGAGGAATATGCCGTA
TTTAAAAGCCTGTCTGAAAGAATCTATGAGGCTTACGCCGAGTGTACCATTTACAACTCGGACTCTTGACA
AGGCAACAGTTCTGGGTGAATATGCTTTACCCAAAGGAACAGTGCTCATGCTAAATACCCAGGTGTTGGGA
TCCAGTGAAGACAATTTTGAAGATTCAAGTCAGTTTAGACCTGAACGTTGGCTTCAGGAGAAGGAAAAAAT
TAATCCTTTTGCGCATCTTCCATTTGGCGTTGGAAAAAGAATGTGCATTGGTCGCCGATTAGCAGAGCTTC
AACTGCATTTGGCTCTTTGTTGGATTGTCCGCAAATACGACATCCAGGCCACAGACAATGAGCCTGTTGAG
ATGCTACACTCAGGCACCCTGGTGCCCAGCCGGGAACTCCCCATCGCGTTTTGCCAGCGATAACTCGAG
```

Figure 12A

```
MSSPISKSRSLAAFLQQLRSPRQPPRLVTSTAYTSPQPREVPVCPLTAGGETQNAAALPGPTSWPLLGSL
LQILWKGGLKKQHDTLVEYHKKYGKIFRMKLGSFESVHLGSPCLLEALYRTESAYPQRLEIKPWKAYRDY
RKEGYGLLILEGEDWQRVRSAFQKKLMKPGEVMKLDNKINEVLADFMGRIDELCDERGHVEDLYSELNKW
SFESICLVLYEKRFGLLQKNAGDEAVNFIMAIKTMMSTFGRMMVTPVELHKSLNTKVWQDHTLAWDTIFK
SVKACIDNRLEKYSQQPSADFLCDIYHQNRLSKKELYAAVTELQLAAVETTANSLMWILYNLSRNPQVQQ
KLLKEIQSVLPENQVPRAEDLRNMPYLKACLKESMRLTPSVPFTTRTLDKATVLGEYALPKGTVLMLNTQ
VLGSSEDNFEDSSQFRPERWLQEKEKINPFAHLPFGVGKRMCIGRRLAELQLHLALCWIVRKYDIQATDN
EPVEMLHSGTLVPSRELPIAFCQR
```

Figure 12B

```
TGGAGAGGGACAGGAGGAAACGCAGCGCCAGCAGCATCTCATCTACCCTCCTTGACACCTCCCCGTGGCT
CCAGCCAGACCCTAGAGGTCAGCCTTGCGGACCAACAGGAGGACTCCCAGCTTTCCCTTTTCAAGAGGTC
CCCAGACACCGGCCACCCTCTTCCAGCCCCTGCGGCCAGTGCAAGGAGGCACCAATGCTCTGAGGCTGTC
GCGTGGTGCAGCGTCGAGCATCCTCGCCGAGGTCCTTTCTGCTGCCTGTCCCGCCTCACCCCGCTCCATC
ACACCAGCTGGCCCTCTTTGCTTCCTTTTCCCAGAATCGTTAAGCCCCGACTCCCACTAGCACCTCGTAC
CAACCTCGCCCCACCCCATCCTCCTGCCTTCCCGCGCTCCGGTGTCCCCCGCTGCCATGAGCTCCCCCAT
CAGCAAGAGCCGCTCGCTTGCCGCCTTCCTGCAGCAGCTGCGCAGTCCGAGGCAGCCCCCGAGACTGGTG
ACATCTACGGCGTACACGTCCCCTCAGCCGCGAGAGGTGCCAGTCTGCCCGCTGACAGCTGGTGGCGAGA
CTCAGAACGCGGCCGCCCTGCCGGGCCCCACCAGCTGGCCACTGCTGGGCAGCCTGCTGCAGATTCTCTG
GAAAGGGGGTCTCAAGAAACAGCACGACACCCTGGTGGAGTACCACAAGAAGTATGGCAAGATTTTCCGC
ATGAAGTTGGGTTCCTTTGAGTCGGTGCACCTGGGCTCGCCATGCCTGCTGGAAGCGCTGTACCGCACCG
AGAGCGCGTACCCGCAGCGGCTGGAGATCAAACCGTGGAAGGCCTATCGCGACTACCGCAAAGAAGGCTA
CGGGCTGCTGATCCTGGAAGGGGAAGACTGGCAGCGGGTCCGGAGTGCCTTTCAAAAGAAACTAATGAAA
CCAGGGGAAGTGATGAAGCTGGACAACAAAATCAATGAGGTCTTGGCCGATTTTATGGGCAGAATAGATG
AGCTCTGTGATGAAAGAGGCCACGTTGAAGACTTGTACAGCGAACTGAACAAATGGTCGTTTGAAAGTAT
CTGCCTCGTGTTGTATGAGAAGAGATTTGGGCTTCTCCAGAAGAATGCAGGGGATGAAGCTGTGAACTTC
ATCATGGCCATCAAAACAATGATGAGCACGTTTGGGAGGATGATGGTCACTCCAGTCGAGCTGCACAAGA
GCCTCAACACCAAGGTCTGGCAGGACCACACTCTGGCCTGGGACACCATTTTCAAATCAGTCAAAGCTTG
TATCGACAACCGGTTAGAGAAGTATTCTCAGCAGCCTAGTGCAGATTTCCTTTGTGACATTTATCACCAG
AATCGGCTTTCAAAGAAAGAATTGTATGCTGCTGTCACAGAGCTCCAGCTGGCTGCGGTGGAAACGACAG
CAAACAGTCTAATGTGGATTCTCTACAATTTATCCCGTAATCCCCAAGTGCAACAAAAGCTTCTTAAGGA
AATTCAAAGTGTATTACCTGAGAATCAGGTGCCACGGGCAGAAGATTTGAGGAATATGCCGTATTTAAAA
GCCTGTCTGAAAGAATCTATGAGGCTTACGCCGAGTGTACCATTTACAACTCGGACTCTTGACAAGGCAA
CAGTTCTGGGTGAATATGCTTTACCCAAAGGAACAGTGCTCATGCTAAATACCCAGGTGTTGGGATCCAG
TGAAGACAATTTTGAAGATTCAAGTCAGTTTAGACCTGAACGTTGGCTTCAGGAGAAGGAAAAAATTAAT
CCTTTTGCGCATCTTCCATTTGGCGTTGGAAAAAGAATGTGCATTGGTCGCCGATTAGCAGAGCTTCAAC
TGCATTTGGCTCTTTGTTGGATTGTCCGCAAATACGACATCCAGGCCACAGACAATGAGCCTGTTGAGAT
GCTACACTCAGGCACCCTGGTGCCCAGCCGGGAACTCCCCATCGCGTTTTGCCAGCGATAATACGCCTCA
GATGGTGGTATTTGCTAACATCATATCCAACTCAGGGAAGCGGACTGAGTGCTGGGATCCAAGGCATTCT
ACAGGGTTCACTGCTGGTTTACACTTCACCTGTGTCAGCACCATCTTCAGGTGCTTAGAATGGCCTGGGA
GCCTGTTCTGTCTTGCATCTTCCATGACATGAAAGGGAGGCTGGCACTTGTCAGTCAGGTAGAGGTTACA
AACCGTTTCAGGCCCTGCCTACCACATTCACTGTTTGAATCTTTAATTCCCAAGAATAAGTTTACATTTC
ACAATGAATGACCTACAACAGCTAAATTTTCTGGGGCTGGGAGTAATACTGACAATCCATTTACTGTAGC
TCTGCTTAATGTACTACTTAGGAAAATGTCCCTGCTTAATAATGTAAGCCAAGCTAAATGATGGTTAAAG
TTATCAGGCCTCCCATGAAATTGCGTTCTTCCTGCATTGAAATAAAAACATTATTGGGAAACTAGAGAAC
ACCTCTATTTTTAAAAGGACTTTAACGAAGTCAAACAACTTATAAGACTAGTGATTCACTGGGCATTAT
TTTGTTAGAGGACCTTAAAATTGTTTATTTTTAAATGTGATTCCTTTATGGCATTAGGGTAAAGATGAA
GCAATAATTTTTAAATTGTGTATGTGCATATGAAGCACAGACATGCATGTGTGTGTGTCTGTGTGTGT
GTGTCCGTGTATGTGTGTGTGGGTTCTAATGGTAATTTGCCTCAGTCATTTTTTTAATATTTGCAGTACT
TGATTTAGGATCTGTGGTGCAGGGCAATGTTTCAAAGTTTAGTCACAGCTTAAAAACATTCAGTGTGACT
TTAATATTATAAAATGATTTCCCATGCCATAATTTTTCTGTCTATTAAATGGGACAAGTGTAAAGCATGC
AAAAGTTAGAGATCTGTTATATAACATTTGTTTGTGATTTGAACTCCTAGGAAAAATATGATTTCATAA
ATGTAAAATGCACAGAAATGCATGCAATACTTATAAGACTTAAAAATTGTGTTTACAGATGGTTTATTTG
TGCATATTTTTACTACTGCTTTTCCTAAATGCATACTGTATATAATTCTGTGTATTTGATAAATATTTCT
TCCTACATTATATTTTTAGAATATTTCAGAAATATACATTTATGTCTTTATATTGTAATAAATATGTACA
TATCTAGGTATATGCTTTCTCTCTGCTGTGAAATTATTTTTAGAATTATAAATTCACGTCTTGTCAGATT
TCATCTGTATACCTTCAAATTCTCTGAAAGTAAAAATAAAAGTTTTTAAATATT    [ SEQ ID NO:3]
```

Figure 13

STABLE CYTOCHROME P450 24 (CYP24) EXPRESSING CELL LINE AND METHODS AND USES THEREOF

RELATED APPLICATION

This application claims the benefit of U.S. provisional patent application No. 60/376,806, filed May 2, 2002, entitled "CYP24 Stable Cell Line For Drug Screening".

FIELD OF THE INVENTION

The invention relates to a stable cell line expressing the cytochrome P450 24 ("CYP24") and methods and uses thereof. It also relates to a recombinant cell that expresses CYP24.

BACKGROUND OF THE INVENTION

The cytochrome P450 s comprise a large gene superfamily that encodes over 500 distinct heme-thiolate proteins that catalyze the oxidation of drugs and numerous other compounds in the body. It is of considerable interest in the pharmaceutical and other fields to identify cytochrome P450 s and the role they play in the metabolism of individual compounds. Cytochrome P450 s are heme—containing enzymes that strongly absorb at a wavelength of 450 nm when the heme is bound to a molecule of carbon monoxide. They are most well known for their ability to catalyze the metabolism of a wide variety of drugs, xenobiotics, carcinogens, mutagens and pesticides, and they are also involved in catalyzing reactions that make or degrade cholesterol, steroids, and other lipids. The reactions performed by these enzymes are generally oxidations, hydroxylations, acetylations, and demethylations. Mutations in cytochrome P450 s or abnormal expression levels can cause a number of human diseases such as glaucoma and breast cancer. Cytochrome P450 s are also involved in the metabolism of a number of vitamins, such as Vitamin A (retinoic acid) [White et. al. (1996) J. Biol. Chem. November, 22: 271(47): 29922-7; WO/97/49815; WO 01/44443] and Vitamin D [Jones, G. et. al. (1999) July; 140(7):3303-10; Dilworth F J, et. al. (1995) Jul. 14; 270(28); 16766-74. In particular, cytochrome P450 s, CYP27 and CYP24, are involved in Vitamin $D_3$ and $D_2$ metabolism. Vitamin $D_3$ and $D_2$, both seco-steroids, are metabolized into their active forms by CYP27 and are then further metabolized by CYP24. CYP24 is a mitochondrial cytochrome P450. that has previously been characterized. For example, isolated human CYP24 was published in Chen et al. (Isolation and expression of human 1,25-dihydroxyvitamin D3 24-hydroxylase cDNA. Proc Natl Acad Sci USA 1993 May 15; 90(10):4543-7). In Chen et al. it was reported that the human 24-hydroxylase 1539 base pair open reading frame encoded a 513 amino acid sequence, 90% homologous to rat CYP24. Mouse CYP24 was characterized in Yoshimura et al. (Molecular cloning of 25-hydroxyvitamin D-3 24-hydroxylase (Cyp-24) from mouse kidney: its inducibility by vitamin D-3. Biochim Biophys Acta 1995 Oct. 17; 1264(1):26-8).

The vitamin D metabolic pathway is part of a vital endocrine system that is highly regulated at certain stages and produces metabolites that control the secretion of the parathyroid gland hormones. $1\alpha,25(OH)_2D_3$, a hormone produced in the vitamin D pathway, regulates phosphate and calcium levels in the blood which in turn control bone mass, the state of bones, and affect cellular differentiation in the skin and the immune system. In the vitamin D pathway, cytochrome P450 s introduce functional groups by hydroxylation usually at positions 1, 25, and 24 of the steroid.

The metabolism of vitamin D begins with 25-hydroxlyation of vitamin $D_3$ or $D_2$ in the liver to $25(OH)D_3$. $25(OH)D_3$ and a second metabolite, $1\alpha,25(OH)_2D_3$, are converted to $24,25(OH)_2D_3$ and $1,24,25(OH)_3D_3$ by CYP24, a mitochondrial P450 involved in the vitamin D pathway. CYP24 is induced by $1,25(OH)_2D_3$ and is found in the kidney as well as other vitamin D target tissues such as the parathyroid cells, keratinocytes, osteoblasts, and enteroctyes.

There are a number Vitamin D related medical conditions. More information on Vitamin D conditions can be found in the Proceedings of the Workshop on Vitamin D (Walter de Gruyter publishing, Berlin), proceedings 1 to 11. For instance, vitamin D deficiency has been related to the following:

(i) in the parathyroid—hyper- and hypo-parathyroidism, Osudohypo-parathyroidism, Secondary hyperparathyroidism;
(ii) in the pancreas—diabetes;
(iii) in the thyroid—medullary carcinoma;
(iv) in the skin—psoriasis;
(v) in the lung—sarcoidosis and tuberculosis;
(vi) in the kidney—chronic renal disease, glomerulonephritis, IgA nephropathy, membraneous nephropathy, glomerulosclerosis, nephrosis, renal insufficiency, hypophosphtatemic VDRR, vitamin D dependent rickets;
(vii) in the bone—anticonvulsant treatment, fibrogenisis imperfecta ossium, osteitits fibrosa cystica, osteomalacia, hypocicemia, osteporosis, osteopenia, osteosclerosis, renal osteodytrophy, rickets;
(viii) in the intestine—glucocorticoid antagonism, idopathic hypercalcemia, malabsorption syndrome, steatorrhea, tropical sprue;
(ix) in the prostate—cancer; and
(x) in the breast—cancer.

More common conditions related to vitamin D or vitamin D metabolite deficiency are obesity problems, hyperhoshatemic turmoral calcinosis, sarcoidosis, tuberculosis, primary hyperparathyroidism, vitamin D dependent rickets type II, cholestatic or paremchymal liver disease.

Excess levels of Vitamin D can be toxic and can cause conditions such as hyperglycemia and mental deficiency. Such conditions usually present themselves upon excess ingestion of Vitamin D.

Since CYP24 is involved in maintaining Vitamin D homeostasis and is implicated in the development of these diseases, it is important to understand how CYP24 activity is and can be modulated in vivo and in vitro. For this, there is a need for a cellular model system that stably expresses CYP24. Such a model system would be especially useful in in vitro drug development studies. To date, there has been no stable cell line expressing CYP24. Cell lines that only generate transient expression are unsuitable for drug development assays. Some cell lines may also not be able to produce active protein (i.e. protein that is folded properly and able to perform a function, the function of native CYP24 such as catalysis). In the absence of a stable cell line, one cannot attribute reduced CYP24 activity to the effects of a candidate inhibitor when it is also possible that the cells merely have lost their ability to express CYP24. There is also a need for a cell model system that not only expresses CYP24 but expresses an active form of the peptide (e.g. that can fold properly and has endogenous CYP24 activities). There is also a need for a cell model system that allows recombinant CYP24 to be active within the cell.

SUMMARY OF THE INVENTION

The invention provides a stable cell line expressing the cytochrome P450 CYP24. The invention also relates to cells and cell cultures of said cell line. The invention further relates to methods and uses of the cell lines.

In one embodiment, the invention provides a cell line that stably expresses CYP24, comprising a recombinant CYP24 nucleic acid molecule that is operably linked to a promoter to enable expression thereof, preferably in biologically active form thereof. In a further embodiment the cells enable CYP24 expression without exogenous cofactors.

In another embodiment the CYP 24 nucleic acid molecule is a nucleic acid molecule that codes for a CYP24 polypeptide. In another embodiment the CYP24 nucleic acid molecule is selected from the group consisting of HPK-1A ras cell CYP24 [SEQ ID NO:1], or one of Genbank Accession Nos. U60669, NT011362, XM030593, AK016668, NM009996, AF312914, NM000782, AL138805, AF245504, AF126400, AF149309, X59506, AH002273, L04619, L4618, L04617, L04616, L04615, L04614 and L04613, Q07973, Q64441, Q09128, $NP_{034126}$, AAA42340, U60669, AH002273 or any DNA sequence encoding an amino acid sequence corresponding to one of the foregoing sequences. In one embodiment, the CYP24 nucleic acid molecule has at least 70% sequence identity to [SEQ. ID. NO. 1], more preferably 90% sequence identity to [SEQ. ID. NO. 1]. In yet another embodiment, the nucleic acid molecule is a homolog, analog, derivative or obvious chemical equivalent, degenerate sequence or mutation that still encodes for CYP24 polypeptide.

In one embodiment the cells of the cell line are mammalian, such as V79 hamster cells, or insect cells, such as SF9 cells.

In another embodiment, the recombinant CYP24 nucleic acid molecule is from a vector comprising CYP24 nucleic acid molecule. For example, said vector can be a plasmid, cosmid, a viral or retroviral vector and selected for optimization with the host cell. In one embodiment, the vector is suitable for transfecting Sf9 cells, such as a baculovirus vector, such as pFastBac1. In another embodiment, the vector is suitable for transforming or transfecting a mammalian cell, such as pcDNA3.1. In one embodiment the vectors further comprise an antibiotic resistance gene, such as neomyocin (neo+) or hygromycin (hygro+) or other marker suitable for selection of transfected or transformed cells.

In one embodiment, the vector is pFBCYP24H6, pFB-CYP24 or pcDNA3.1-CYP24H6 or pcDNA3.1-CYP24. In another embodiment the pcDNA3.1 is neo+ or hygro+.

In another embodiment, the cell line is derived from Sf9 cells transfected with pFBCYP24H6 or pFBCYP24, preferably pFBCYP24H6. In a further embodiment, the cell line is derived from V79 hamster cells transformed with pcDNA3.1-CYP24 or pcDNA3.1-CYP24H6, more preferably pcDNA3.1-CYP24.

In another embodiment, the invention provides a method of making a cell line of the invention expressing CYP24 comprising:

(i) isolating a suspension of cells, (ii) inserting in the cells a recombinant gene encoding CYP24 so that it is operably linked to a promoter and a selectable marker, such as, but not limited to an antibiotic resistant gene, to produce a culture containing cells that comprise said recombinant gene, and (iii) enriching the culture by selectably growing cells expressing CYP24 in media differentially favorable for growth of the cells expressing CYP24, to obtain a cell line expressing CYP24.

The invention includes a cell culture comprising cells of the invention. The cells stably express CYP24 and include a recombinant CYP24 nucleic acid molecule that is operably linked to a promoter to enable expression thereof, in a medium capable of sustaining growth and replication of the cells.

In another embodiment, the invention provides a method of identifying a modulator of a CYP24 polypeptide comprising, (i) culturing the cell line that stably expressed CYP24 of the invention under conditions wherein the cell expresses the polypeptide CYP24 in the presence of a CYP24 substrate and a candidate modulator; and (ii) determining whether the candidate modulator modulates CYP24 substrate activity, wherein increased or decreased CYP24 activity indicates that the candidate modulator is a modulator of the CYP24 polypeptide.

In an embodiment, the CYP24 activity is monitored by one or more of the following:

a. monitoring binding of the candidate modulator with the substrate;

b. monitoring of CYP24 induced substrate metabolites;

c. monitoring binding of CYP24 with the candidate modulator; and/or d. monitoring CYP24 gene expression.

In a further embodiment of the method for identifying the modulator, the effect of the candidate modulator is determined by comparing the affect of said candidate modulator with that of a control. For instance, the control can comprise conducting the method in the absence of the candidate modulator or in the presence of a positive control such as ketoconazole, a known CYP24 inhibitor.

In the method of identifying the modulator, in an embodiment, the step of determining whether the candidate compound modulates CYP24 polypeptide activity comprises adding a substrate to the cell and detecting increased or decreased activity of the CYP24 on the substrate in the presence of the candidate compound.

In another embodiment, the cell line can be used for generating CYP24 comprising culturing said cell line under conditions that enable and/or promote CYP24 expression. In a further embodiment the cells of the invention are cultured under conditions that enable CYP24 activity. A method of isolating CYP24 comprising expressing CYP24 in a cell line of the invention and isolating the expressed CYP24 is also herein provided.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Embodiments of the invention will be described in relation to the drawings in which:

FIG. 12A Nucleic acid coding region sequence [SEQ ID NO:1] (1560 bp)—amplified region of CYP24 for stable cell line construct. The sequence for CYP24 in pcDNA3.1-hygro (+) is the coding sequence of CYP24 with GCTAGCACC at 5' end (the first six nucleotides are for NheI site [SEQ. ID. NO. 9]) before ATG and CTCGAG [SEQ. ID. NO:10] after stop codon TAA at 3' end (the sequence for XhoI site). The sequence corresponds to Genebank Accession no. (NCBI) XM_030593.

FIG. 12B. Amino acid sequence [SEQ ID NO: 2]—gi|14786394|ref|XP_030593.1| cytochrome P450, subfamily XXIV precursor [*Homo sapiens*].

FIG. 13. Full length *homo sapiens* nucleic acid sequence CYP24 (3274 bp) [SEQ ID NO:3]>gi|14786393|ref|XM_030593.1| *Homo sapiens* cytochrome P450, subfamily XXIV (vitamin D 24-hydroxylase) (CYP24), mRNA.

DETAILED DESCRIPTION OF THE INVENTION

Figure 1:
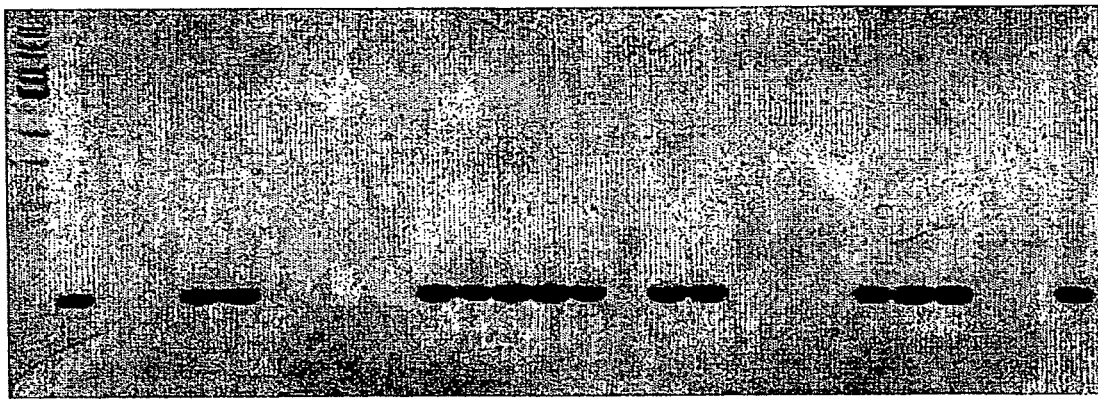
FIG. 1 RT-PCR analysis of single-cell cloned CYP24/V79 cells.

The invention satisfies the need for a stable cell line expressing the cytochrome P450 CYP24.

"Cell line" as used herein means a population or mixture of cells of common origin growing together after several passages in vitro. By growing together in the same medium and culture conditions, the cells of the cell line share the characteristics of generally similar growth rates, temperature, gas phase, nutritional and surface requirements. The presence of cells in the cell line expressing CYP24 can be ascertained, provided a sufficient proportion, if not all, of cells in the line are present to produce a measurable quantity of the substance. An enriched cell line is one in which cells having certain trait e.g. expression of CYP24, are present in greater proportion after one or more subculture steps than the original cell line. Preferably the cell line is derived from one, two or three originating cells. The cell line can become more homogenous with successive passages and selection for specific traits. Clonal cells are those which are descended from a single cell.

"Recombinant cell" as used herein means a cell that has been genetically modified from its native form by way of transfection with a foreign (non-endogenous) genetic (nucleic acid) material.

A cell line or cell comprising a recombinant CYP24 nucleic acid molecule is a cell line or cell that comprises a CYP24 nucleic acid molecule that is not endogenous to said cell line or cell, as the case may be. The cell line or cell preferably produces no or low endogenous CYP24 expression. The cell line is stable in that it expresses CYP24 for more than a transient period of time. The stable cell line should express CYP24 for a minimum of at least one month, and preferably at least two months, at least four months and most preferably at least 6 months or 12 months. The CYP24 produced by the cells is biologically active in that metabolizes $25(OH)D_3$ and $1\alpha,25(OH)_2D_3$, to $24,25(OH)_2D_3$ and $1,24,25(OH)_3D_3$. The cell lines of the invention are preferably immortalized. The cells are optionally subcultured periodically, such as about once every three days. The cells are also optionally passaged at least 20 times, at least 40 times or at least 100 times. Certain diseases cause mammals to express significantly altered levels of CYP24 protein and mRNA levels encoding CYP24 protein when compared to a corresponding "standard" mammal i.e., a mammal of the same species not having the condition. Cancer would be one example of where CYP24 levels are increased. In other conditions, CYP24 levels may be decreased or insufficient.

The stable cell lines of the invention are very useful to identify modulators to inhibit or activate CYP24 to treat these conditions. Since CYP24 expression is consistent for a prolonged period of time in the stable cell line of the invention, a researcher can reliably attribute modulation of CYP24 activity to the activating or inhibiting effects of a candidate compound.

"Regulatory elements" or "Regulatory sequences" as used herein means those elements or sequences in addition to those directly coding for the amino acid sequence in question that regulate the expression of the amino acid sequence in question. Such elements or sequences include, but are not necessarily limited to: promoters, operons or other sequences that need to be operably linked to the CYP24 nucleic acid molecule to enable expression or regulation of expression of CYP24.

"Modulator" as used herein means any substance (e.g. drug, chemical, peptide, antibody, nucleic acid molecule) or condition (temperature, salt levels, pH, etc.) that can increase, decrease or maintain (e.g. homeostasis—increase or decrease as required) CYP24 expression or activity. These can include any agonist, antagonist or simulator.

"CYP24 peptide, polypeptide or protein" is an amino acid sequence from a family of cytochrome P450's that catalyses the following reaction: Vitamin D metabolites—$25(OH)D_3$ and $1\alpha,25(OH)_2D3$, to $24,25(OH)_2D_3$ and $1,24,25(OH)_3D_3$, respectively. As used herein, "CYP24" or "CYP24 peptide", "CYP24 polypeptide" or "CYP24 protein" are used interchangeably." has the amino acid sequence as shown in SEQ. ID. NO. 2 or that of a homolog, a species homolog, analog, or derivative of SEQ. ID. NO. 2 that has the above-noted enzymatic activity. "CYP24" also includes a biologically active fragment or obvious chemical equivalent of SEQ. ID. NO. 2, homolog, species homolog, analog or derivative thereof.

CYP24 polypeptide may include various structural forms of the primary protein that retain biological activity. For example, a polypeptide of the invention may be in the form of acidic or basic salts or in neutral form. The CYP24 polypeptides may be modified by either natural processes, such as post-translational processing or by chemical modification techniques, which are well known in the art. Such modifications are described in basic texts, research manuals and research literature. Modifications may occur anywhere in the CYP24 including the peptide backbone, the amino acid side-chain and the amino or carboxyl termini. It will be appreciated that the same type of modification may be present in the same or varying degree at several sites in a given CYP24 polypeptide. In addition, a given CYP24 may contain many types of modification. The modifications may result from post-translational natural processes or may be made by synthetic methods.

The term "analog" includes any polypeptide such as CYP24 having an amino acid residue sequence substantially identical to the CYP24 sequences described in this application in which one or more residues have been conservatively substituted with a functionally similar residue and which displays CYP24 activity as described herein. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" refers to a polypeptide such as CYP24 derivative having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5 hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

"Obvious chemical equivalent" as used herein means a compound (e.g. nucleic acid molecule, peptide, or other compound) or a method of making stable CYP24 cells or using stable CYP24 cells that has no material effect on the way that the invention works. The fact that the variant has no material effect will be obvious to a reader skilled in the art. Examples of obvious chemical equivalents include but are not limited to obvious variations of CYP24, degenerate CYP24 nucleic acid sequences, vectors or reagents and conservative amino acid substrates of CYP24.

"Sequences having substantial sequence homology" means those polypeptide or nucleic acid sequences which have slight or inconsequential sequence variations from [SEQ ID NOS:1-3] or one of the other sequences described in this application, i.e., the sequences function in substantially the same manner and, with respect to nucleic molecules code for functionally equivalent proteins. The variations may be attributable to local mutations or structural modifications.

The peptides of the invention can be isolated from cells expressing said polypeptide using techniques known in the art. In another embodiment, the peptides of the invention can be synthetically made using techniques known in the art.

CYP24 Nucleic Acids

CYP24 nucleic acid is a family of nucleic acid cytochrome P450's that includes many types of CYP24 nucleic acids. As used herein, a CYP24 nucleic acid is a nucleic acid molecule that codes for CYP24 polypeptide as defined above. A preferred CYP24 nucleic acid is the isolated cDNA sequence obtained by RT-PCT of the CYP4 mRNA from the HPK-1A ras cell CYP24 [SEQ ID NO:1] (FIG. 12A). The corresponding amino acid sequence is shown as [SEQ ID NO:2] (FIG. 12B) and the full length nucleic acid sequence is shown as [SEQ ID NO:3] (FIG. 13) CYP24 may be obtained from other sources, such as the sequences in Genbank Accession Nos. U60669, NT011362, XM030593, AK016668, NM009996, AF312914, NM000782, AL138805, AF245504, AF126400, AF149309, X59506, AH002273, L04619, L4618, L04617, L04616, L04615, L04614, L04613, Q07973, Q64441, Q09128, NP034126, AAA42340, U60669 or AH002273. Any DNA sequence encoding an amino acid sequence corresponding to one of the foregoing sequences would be useful. Any nucleic acid sequence encoding a polypeptide corresponding to one of the above-encoded sequences would be useful.

Thus, a CYP24 "nucleic acid" refers to isolated nucleic acids which encode CYP24 clone peptides and to obvious chemical equivalents thereof, including degenerate nucleic acid sequences.

A CYP24 "nucleic acid" also refers to isolated nucleic acids which encode the amino acid sequence in [SEQ ID NO:1 or 3], or a biochemically active fragment thereof.

CYP24 "nucleic acid" also includes polynucleotides comprising nucleic acid sequences having substantial sequence homology with the sequences of SEQ. ID. NOS. 1 or 3. Preferably, nucleic acids are capable of hybridizing, under stringent hybridization conditions, to [SEQ ID NO:1 or 3], or the complement thereof. "Stringent hybridization conditions" refers to an overnight incubation at 42° C. in a solution comprising 50% formamide, 5×SSC [750 mM NaCl, 75 mm sodium citrate], 50 mM sodium phosphate [pH 7.6], 5× Denhardt's solution, 10% dextran sulfate, and 20 ug/ml denatured, sheared salmon sperm DNA, followed by washing the filters in 0.1×SSC at about 65° C.

In addition, CYP24 nucleic acids may contain one or more modified bases or DNA or RNA backbones modified for stability or for other reasons. "Modified" bases include, for example, tritiated bases and unusual bases such as inosine. A variety of modifications can be made to DNA and RNA; thus, "nucleic acid" embraces chemically, enzymatically, or metabolically modified forms.

CYP24 nucleic acids also include variants having at least: 60%, 70%, 80%, 90%, 95%, 96%, 97%, 98% or 99% sequence identity to [SEQ ID NO:1 or 3] that code for a CYP24 polypeptide. Sequence identity can be determined conventionally using known computer programs. A preferred method for determining the best overall match between [SEQ ID NO:1 or 3] a subject sequence, also referred to as a global alignment, can be determined using the FASTDB computer program based on the algorithm of Brutlag et al., Comp. App. Biosci. 6: 237-245 (1990). In a sequence alignment, the query and the subject sequence are both DNA sequences. An RNA sequence can be compared by converting U's to T's. The result of said global sequence alignment is in percent identity. Preferred parameters used in a FASTDB alignment of DNA sequences to calculate percent identity are: Matrix-Unitary, k-tuple=4, Mismatch Penalty=1, Joining Penalty=30, Randomization Group Length=09, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the result. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specific parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated from the purposes of manually adjusting the percent identity score.

Also provided in the present invention are homologs of CYP24, such as species homologs. Species homologs may be isolated and identified by making suitable probes or primers from the sequences provided herein and screening a suitable nucleic acid source for the desired homolog.

CYP24 nucleic acids and polypeptides can be obtained using techniques known in the art. Such methods include isolating naturally occurring polypeptides and polynucleotides, recombinantly or synthetically/chemically produced polynucleotides or polypeptides or a combination of these methods.

An isolated CYP24 nucleic acid molecule which comprises DNA can be isolated by preparing a labeled nucleic acid probe based on all or part of the nucleic acid sequences as shown in [SEQ. ID. NOS. 1 or 3] and using this labeled nucleic acid probe to screen an appropriate DNA library (e.g. a cDNA or genomic DNA library). For example, a genomic library isolated can be used to isolate a DNA encoding a CYP24 protein by screening the library with the labeled probe using standard techniques. Nucleic acids isolated by screening of a cDNA or genomic DNA library can be sequenced by standard techniques.

An isolated CYP24 nucleic acid molecule, which is DNA, can also be isolated by selectively amplifying a nucleic acid encoding a CYP24 protein using the polymerase chain reaction (PCR) methods and cDNA or genomic DNA. It is possible to design synthetic oligonucleotide primers from the nucleic acid sequence as shown in [SEQ. ID. NOS. 1 or 3] for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis.

A CYP24 isolated nucleic acid molecule, which is RNA, can be isolated by cloning a cDNA encoding a novel protein of the invention into an appropriate vector, which allows for transcription of the cDNA to produce an RNA molecule, which encodes a protein of the invention. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A CYP24 nucleic acid molecule may also be chemically synthesized using standard techniques (eg, Wendell McKenzie. DNA Synthesis. (1994, Gordon and Breach Publishing Group, USA)). Various methods of chemically synthesizing polydeoxynucleotides are known, including solid-phase synthesis, which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes CYP24 may be accomplished by expressing the cDNA in an appropriate host cell by standard techniques, and testing the activity of the protein using the methods as described herein. A cDNA having the activity of a CYP24 protein so isolated can be sequenced by standard techniques, such as dideoxynucleotide chain termination or Maxam-Gilbert chemical sequencing or by automated DNA sequencing, to determine the nucleic acid sequence and the predicted amino acid sequence of the encoded protein.

An "anti-sense CYP24 nucleic acid" as used herein is a nucleotide sequence that is complementary to a target, preferably CYP24 mRNA or DNA. In another embodiment the antisense sequence targets part of the mRNA or DNA encoding CYP24. Preferably, an antisense sequence is constructed by inverting a region preceding or targeting the initiation codon or an unconserved region. In particular, the nucleic acid sequences contained in the nucleic acid molecules of the invention or a fragment thereof, preferably a nucleic acid sequence shown in [SEQ. ID. NOS. 1 or 3] may be inverted relative to their normal presentations for transcription to produce antisense nucleic acid molecules. In one embodiment the antisense molecules can be used to inhibit CYP24 expression.

Stable CYP24 Cells

CYP24 nucleic acid molecules may be incorporated into an appropriate, commercially available expression vector according to procedures known in the art in order to ensure good expression of the protein in a host cell. Such vectors may be viral, retroviral, plasmids, and cosmids. It is also known in the art that the selection of a suitable vector will also depend on the host cell selected and vise versa. It is known in the art that certain vectors are more suitable with certain host cells. For instance, it is known that baculovirus vectors, such as pFastBac1 work well in insect cell lines, such as Sf9 and plasmids such as pcDNA3.1, pcDNA 3.1-Hygro(+) work well in mammalian cells, such as V79 hamster cells. One example uses the commercially available plasmid pFastBac1 to make pFB-CYP24H6 or pFBCYP24. These were then used to transfect sF9 cells to get an SF9 CYP24 and CYP24H6 expressing stable cell line (baculoviruses expressing CYP24 and CYP24H6). For Sf9 cells, the amount of virus used relative to the number of cells and the infection time will affect the expression level of CYP24. In another embodiment, pcDNA3.1-CYP24 and pcDNA3.1-CYP24H6 were made and used to transform V79 cells, to create V79 CYP24 and CYP24H6 expressing stable cell line. Another vector used was pBS-H6 to make pBSCYP24H6. The invention includes a recombinant expression vector containing CYP24 nucleic acid and the necessary regulatory sequences for production of CYP24 in a stable cell line. Suitable regulatory sequences may be derived from a variety of sources, including bacterial, fungal, or viral genes (for example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Mammalian and insect cells are preferred host cells. V79 hamster cell is an example of a suitable mammalian cell. Sf9 is an example of a suitable insect cell. Both V79 and Sf9 cells are readily available from commercial cell suppliers, such as the ATCC and other tissue culture collections. Other suitable host cells are readily apparent and available to those skilled in the art. Suitable cells for transfection preferably have no or low endogenous levels of CYP24 to enable one to monitor the affect of certain factors (including candidate chemical modulators), on CYP24 expression and/or activity. Preferred cell lines express the cofactors necessary for CYP24 activity such as adrenodoxin (ADX) and adrenodoxin reductase (ADR).

"Conditions suitable for CYP24 expression" as used herein means the culture conditions, be it media, the presence of substrate or cofactors, pH, temperature or other environmental conditions that are required for CYP24 expression.

In one embodiment, the expressed CYP24 incorporates into the mitochondrial membrane of the host cell and the addition of exogenous cofactors such as NADPH, ADR and/or ADX is not required for CYP24 activity. In another embodiment, exogenous NADPH, ADX and ADR are added to the cells to enhance CYP24 activity. Recombinant CYP24 in active form is also produced without addition of cofactors (endogenous cofactors in the cell are used).

In another embodiment, the cell lines of the present invention can be a source of CYP24. CYP24 can be isolated therefrom using techniques known in the art.

CYP24 Modulators

This invention further provides methods for screening compounds to identify modulators, e.g. activators and inhibitors of CYP24 and its variants. Inhibitors include antibodies, drugs, small molecules, peptides, or in some cases, oligonucleotides. An activator is a compound that enhances the function or increases the levels of polypeptide. Inhibitors block the function or decrease the levels of polypeptide. Modulators also include agonsists, antagonists of CYP24 expression and/or activity.

CYP24 activity can be directly inhibited by the binding of a small molecule or drug. The present invention thus includes a method of screening drugs, chemicals, compounds (novel and/or known compounds) for their effect on activity and/or expression (i.e., as a modulator) of CYP24 polypeptide. In particular, modulators of CYP24 activity, such as drugs or peptides, can be identified in a biological assay by expressing CYP24 in a cell, adding a substrate and detecting activity of CYP24 polypeptide on the substrate in the presence or absence of a modulator. In other instances, the substrate is added to induce CYP24 expression in the presence or absence of a candidate modulator. Thus, the CYP24 protein can be exposed to a candidate compound and the effect on protein activity can be determined. Prospective drugs can be tested for modulation of the activity of other P450 cytochromes, which are desired not to be modulated. In this way, drugs that selectively modulate CYP24 over other P450 s can be identified.

The effect on CYP24 expression and/or activity can be determined using techniques known in the art. For instance, affect on CYP24 expression can be monitored by monitoring the presence and/or levels of CYP24 mRNA. The effect on CYP24 activity can be monitored by monitoring the presence and/or levels of substrate metabolite(s). This can be monitored in reference to controls. The controls can be positive or negative controls. It could be external and/or internal controls. For instance, activity and/or expression levels of a candidate modulator can be ascertained by comparing said levels with an assay done in the presence of a known modulator (activator or inhibitor, as the case may be), in the absence of a modulator (on the same cells or parallel cell lines), in cells that endogenously express CYP24 (e.g. Human ras K cells). Binding of a candidate modulator with the substrate in the presence/absence of CYP24 also indicate potential modulating activity. Similarly binding of the candidate modulator with CYP24 in the presence of the substrate, is also indicative of modulating activity. Such binding assays are well known in the art. Potential modulators of CYP24 activity are CYP24 cofactors or combinations thereof such as the addition of both ADX and ADR enhances CYP24 expression in the cell line of the present invention.

A potential inhibitor is a peptide derivative of CYP24 (e.g. a naturally or synthetically modified analog) that has lost catalytic function yet still recognizes CYP24 substrates. Examples of peptide derivatives include, but are not limited to, small peptides or peptide-like molecules. An inhibitor could also be a Vitamin D analog or derivative that competes with Vitamin D for binding with CYP24.

Antisense constructs prepared using antisense technology are also potential inhibitors. Therefore, the present invention is further directed to inhibiting polypeptide in vivo by the use of antisense technology. [for example, antisense-Okano, J. Neurochem. 56: 560 (1991); Oligodeoxynucleotides as Antisense Inhibitors of Gene Expression, CPR Press, Boca Raton, Fla. (1988)]. A DNA oligonucleotide is designed to be complementary to a region of the gene involved in transcription [triple-helix, see Lee et al., Nucl. Acids Res. 6: 3073 (1979); Cooney et al., Science 241: 456 (1988); and Dervan et al., Science 251: 1360 (1991)], thereby preventing transcription and the production of the CYP24 polypeptides.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

Antibodies to CYP24 and or substrate may also inhibit CYP24 activity.

Modulators may also be designed using CYP24 peptide and/or substrate structure information.

Pharmaceutical Compositions

There are diseases or conditions in which a subject is administered a pharmaceutical composition comprising an effective amount of a compound that inhibits CYP24 expression or activity. An inhibitor identified using the stable cell line is optionally administered in combination with 1,25 vitamin D3. The inhibitor will allow the active vitamin D to exert its effect.

The pharmaceutical compositions for administration to subjects are formulated in a biologically compatible composition suitable for administration in vivo. As used herein "biologically compatible form suitable for administration in vivo" means a form of the substance to be administered in which therapeutic effects outweigh any toxic effects. The substances may be administered to animals in need thereof.

The pharmaceutical composition will be formulated and dosed in a fashion consistent with good medical practice, taking into account the clinical condition of the individual patient (and potential side effects), the site of delivery, the method of administration, the scheduling of administration, and other factors known to practitioner. Administration of a "therapeutically effective amount" of pharmaceutical compositions of the present invention is defined as an amount of the pharmaceutical composition, at dosages and for periods of time necessary to achieve the desired result. For example, a therapeutically active amount of a substance may vary according to factors such as disease state, age, sex, and weight of the recipient, and the ability of the substance to elicit a desired response in the recipient. Dosages may be adjusted to provide an optimum therapeutic response. For example, several divided doses may be administered daily or the dose may be proportionally reduced as indicated by the exigencies of the therapeutic situation. Subject to therapeutic discretion, preferably dosages of administration of active compound will be in the range of about 1 μg/kg/day to 10 mg/kg/day of patient body weight and most preferably at least 0.01 mg/kg/day, and most preferably for humans between about 0.01 and 1 mg/kg/day.

An active substance may be administered in a convenient manner such as by injection (subcutaneous, intravenous, topical, intratumoral etc.), oral administration, inhalation, transdermal application, or rectal administration. Depending on the route of administration, the active substance may be coated in a material to protect the compound from the action of enzymes, acids and other natural conditions which may inactivate the compound, prior to reaching the desired site of delivery. It can also be formulated into a sustained release composition.

The compositions described herein can be prepared by known methods for the preparation of pharmaceutically acceptable compositions which can be administered to subjects, such that an effective quantity of the active substance is combined in a mixture with a pharmaceutically acceptable carrier. Suitable carriers are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Recombinant nucleic acid molecules comprising a sense, an antisense sequence or oligonucleotide fragment thereof, may be directly introduced into cells or tissues in vivo using delivery vehicles known in the art such as retroviral vectors, adenoviral vectors and DNA virus vectors. They may also be introduced into cells in vivo using physical techniques known in the art such as microinjection and electroporation or chemical methods such as coprecipitation and incorporation of DNA into liposomes. Recombinant molecules may also be delivered in the form of an aerosol or by lavage.

EXAMPLES

The following non-limiting examples are illustrative of the present invention:

Example 1

Generation of Expression Vectors with Full-length CYP24 cDNA

HPK-1A ras cells were treated with 10 nM 1,25(OH)$_2$D3 for 18 hours. Cells were collected and total RNA was prepared using Trizol reagent. The full-length CYP24 cDNA was amplified using one-step RT-PCR kit (Clontech) according to the protocol suggested by the supplier. The forward primer used is 5'-TAC GCTAGCACCATGAGCTCCCCCATCAGCAA-3' (SEQ. ID. NO. 4) and the reverse primer used is 5'-AGG CTCGAGTTATCGCTGGCAAAACGCGATGG-3' (SEQ. ID. NO. 5) An NheI site and an XhoI site (underlined) were engineered in the forward and the reverse primer before the start codon and after the stop codon, respectively. The 1570 bp PCR fragment was digested with NheI and XhoI and the 1560 bp NheI-XhoI fragment was cloned into the mammalian expression vector pcDNA3.1-Hygro(+) (Invitrogen) that had been digested with the same enzymes. The ligation was used to transform E. coli TOP 10 cells (Invitrogen) and the transformed cells were incubated at 30° C. overnight. The recombinant pcDNA3.1-CYP24 was screened and the fidelity of the PCR fragment was confirmed by sequencing.

To generate the his-tagged version of CYP24, the C-terminal portion of the gene was amplified by PCR using the full-length cDNA cloned in pcDNA3.1 as template. The forward primer used is 5'-CCCAAAGGAACAGTGCT-CATGC-3' (nt 1228-1249) (SEQ. ID. NO. 6) and the reverse primer used is 5'-TGG CTCGAGTCGCTGGCAAAACGCGATGGGG-3' (SEQ. ID. NO. 7) The reverse primer removes the stop codon and has an XhoI site (underlined). The 320 bp PCR fragment was digested with BamHI and XhoI and the 280 bp BamHI-XhoI fragment was cloned into the tagging vector pBS-H6 that had been digested with BamHI and SalI. The fidelity of the PCR fragment was confirmed by sequencing. This resulted in the addition of 8 amino acids, VDHHHHHH [SEQ. ID. NO. 8], at the C-terminus of CYP24. Then the resulting vector was digested with BamHI and XhoI and the 300 bp BamHI-XhoI fragment was recovered and ligated to the backbone of pcDNA3.1-CYP24 that had been digested with the same enzymes. Subsequently, the his-tagged full-length cDNA was excised and cloned into the donor plasmid pFastBac1 to give pFB-CYP24H6.

Example 2

Expression of CYP24 in Sf9 Insect and V79 Hamster Cells

The recombinant donor plasmid, pFB-CYP24H6, was used to generate baculovirus encoding his-tagged CYP24, according to the suggestions of the supplier (Gibco Life Technology). The expression of his-tagged CYP24 was confirmed by immunoblotting on whole cell lysate. The virus was expanded and titration determined.

To generate a stable V79 cell line for CYP24, pcDNA3.1-CYP24 was maxi-prepared and used to transfect V79 hamster cells using FuGENE reagent (Roche) as recommended by the supplier. The transfected cells were selected for two weeks in the presence of 100 μg/ml hygromycin before being single-cell cloned into 96-well plate (seed 50 cells per plate) to isolate the expression clones. Thirty populations of cells derived from a single cell in the 96-well plate were expanded into 6-well plate. Total RNA was later isolated from 24 expanded clones using Trizol reagent. RT-PCR analysis was performed using one-step RT-PCR kit (Clontech) and 13 positive clones (# 2, 3, 9, 10, 11, 13, 14, 16, 17, 21, 22, 23, and 26) were expanded and stocks prepared.

Example 3

Requirements of Co-factors for His-tagged CYP24 Expressed in Insect Sf9 Cells

To examine the effect of co-factors on the activity of CYP24, recombinant baculoviruses encoding his-tagged adrenodoxin (ADX), adrenodoxin reductase (ADR), or both were generated. His-tagged CYP24 was expressed in insect cells either alone, or with adrenodoxin, adrenodoxin reductase, or both. Three hundred ml of Sf9 cells (0.8 million cells/ml) in TNM-FH medium (BD Pharmingen) were cultured in roller bottles in the presence of 2 μg/ml hemin chloride, 100 μM δ-amino-levulinic acid, and 100 μM ferric citrate. Baculoviruses encoding his-tagged CYP24 and co-factors were added at multiplicity of infection of 2. The cells were collected 66-70 hours after infection and the mitochondrial fraction was prepared as described below.

Preparation of Mitochondrial Fraction

In one example, cells are placed in cold MT buffer (100 mM potassium phosphate buffer, pH 7.5, and 0.25 M sucrose) and transferred to 50 ml tubes. The cells are centrifuged at 800 g for 10 min at 4° C. and the supernatant is discarded. Protease inhibiting tablet is dissolved in MT buffer (one tablet/10 ml of MT buffer). $CaCl_2$ is added to 0.25 mM and the mix is vortexed to suspend cells in the buffer, with about 10 ml per 150 million Sf9 cells. Cells are transferred into the chamber of pre-cooled nitrogen bomb. The cells are equilibrated for 10 minutes under pressure of 300 psi. Cells are slowly released from the bomb into the 50 ml tube. Repeat the nitrogen bomb steps. EGTA is added to 1 mM final. The mix is centrifuged at 800 g for 10 minutes at 4° C. The supernatant is combined in a Beckman 50 ml tube for JA20 rotor. The pellet is washed once with 10 ml MT buffer and the supernatants combined together followed by centrifugation at 10,000 g for 10 minutes at 4° C. The supernatant is discarded and the pellet washed once with 20 ml of MT buffer followed by centrifugation again at 10,000 g for 10 min at 4° C. The supernatant is discarded. The tube is drained by inverting the tube on paper tower for a minute. One ml of MT buffer is added to the tube. The mitochondrial fraction (pellet) is homogenized. The protein concentration of the mitochondrial fraction is determined. Samples are diluted to 5 mg/ml. Immunoblotting is done with 10 μl of sample and store the rest in cryogenic vials at −70° C. freezer until needed. CYP24 expressing mitochondria retain full function after being stored at −70° C. for three months.

Figure 2:
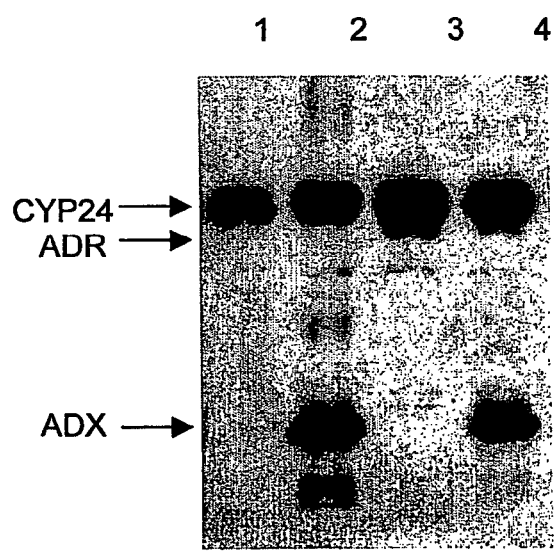
FIG. 2 Levels of CYP24 expression in isolated mitochondria.

The expression levels of his-tagged CYP24 in isolated mitochondria were determined by immunoblotting. Mitochondrial protein was diluted to 0.2 μg/μl with MT buffer and an equal amount of 2 times SDS loading buffer was added. Samples were mixed and heated at 100° C. for 5 min. Ten μl of each sample was loaded on 12.5% SDS-PAGE. Separated proteins were transferred to polyvinylidene fluoride (PVDF) membrane and expression of his-tagged CYP24 and co-factors was detected using anti-his antibody (FIG. 2). The results showed that CYP24 was expressed at comparable levels under these conditions.

Primary antibody: monoclonal Penta-His antibody (QIAGEN) used at 0.1 ng/ml.

Secondary antibody: HRP conjugated goat anti mouse Ig used at 1:10,000.

CYP24 activity in these four samples was determined. Mitochondrial fraction prepared from Sf9 cells infected with a control virus was also included. Two hundred μg of mitochondrial protein was used in each assay in 200 μl in the presence of 100 mM potassium phosphate, pH 7.5, 250 mM sucrose, 1 mM DTT, 1 mM EDTA, 5 mM $MgCl_2$, 1 mM NADPH, 5 mM D, L-trisodium isocitrate, and 0.2 units of isocitrate dehydrogenase. The reaction was started by adding 50,000 CPM of [$^3$H-1β]-1,25(OH)$_2$D3 in 1 μl of ethanol. The reaction was carried out at 37° C. for 15 min. Then the reaction was extracted using Bligh-Dyer extraction method (see below). The radioactivity present in the aqueous phase was counted and the percentage of conversion was calculated as following:

Percentage of conversion=[(total aqueous *CPM* in sample tube)−(total aqueous *CPM* in control tube)]*100%/(total *CPM* added)

The Bligh-Dyer extraction method is preferred. An example of volumes of reagents is provided for 200 μl of reaction. First, 5 μl of 10% acetic acid and 0.5 ml of methanol are added to each tube (well). Dichloromethane (0.25 ml) is added to each tube and vortexed for 30 s. Next, 0.25 ml of dichloromethane is added followed by 0.25 ml of saturated KCl. The mix is spun at 4,000 rpm for 10 min. Next, 100 μl of the aqueous phase (top, total 950 μl) is used for radioactivity counting and the rest of the aqueous phase is aspirated. The organic phase (bottom) is vacuum dried then d dissolved in 150 μl mobile phase and spun at 10,000 rpm for 5 min. Next, 140 μl of sample is transferred to the insert for HPLC analysis.

Figure 3:
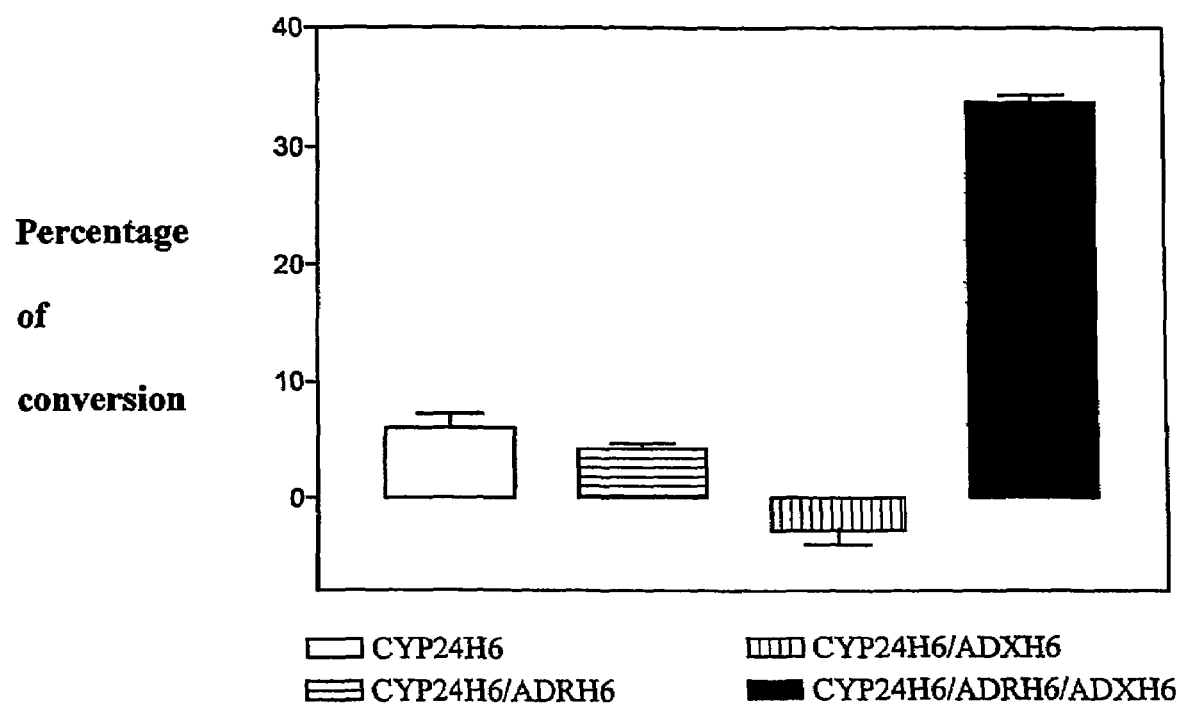
FIG. 3 Effect of co-factors on CYP24 activity.

The results showed that mitochondria from Sf9 cells could support the function of CYP24 (FIG. 3). The presence of adrenodoxin reductase had no significant effect on CYP24 activity, while co-expression of adrenodoxin somehow suppressed CYP24 activity. However, in the presence of both co-factors, CYP24 activity increased 4-5 fold.

Example 4

Screening of Stable CYP24/V79 Transfectants with High Enzymatic Activity

Cells of the 13 RT-PCR positive CYP24/V79 clones were further screened by CYP24 activity assay. Cells were seeded in duplicate in 6-well plate (for initial screening, cell number is not standardized). No cell and V79 cell controls were also included in the assay. After 18 hours, 1 μl of [$^3$H-1β]-1,25(OH)$_2$D3 (50,000 CPM/μl) in ethanol was added to each well and incubated for 24 hours. Cells were then extracted with Bligh-Dyer method. The radioactivity present in the aqueous phase was counted. The percentage of conversion for each clone was calculated as following:

Percentage of conversion=[(total CPM in sample well)−(total CPM in no cell control well)] *100%/(total CPM added)

Figure 4:
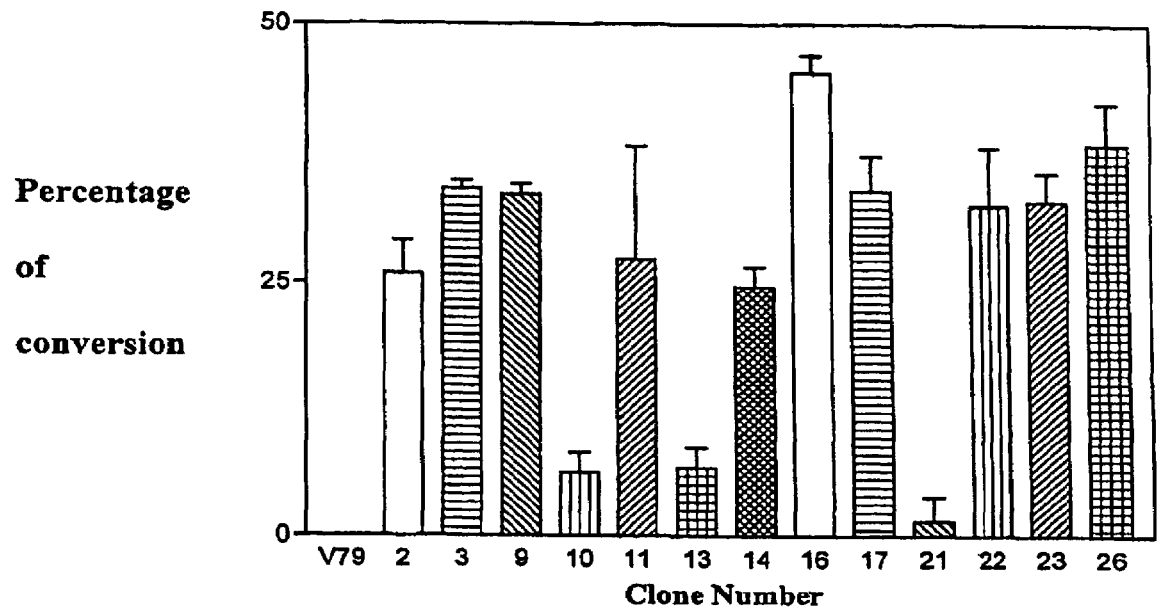
FIG. 4 CYP24 activity in single-cell cloned CYP24/V79 cells.
Figure 5:
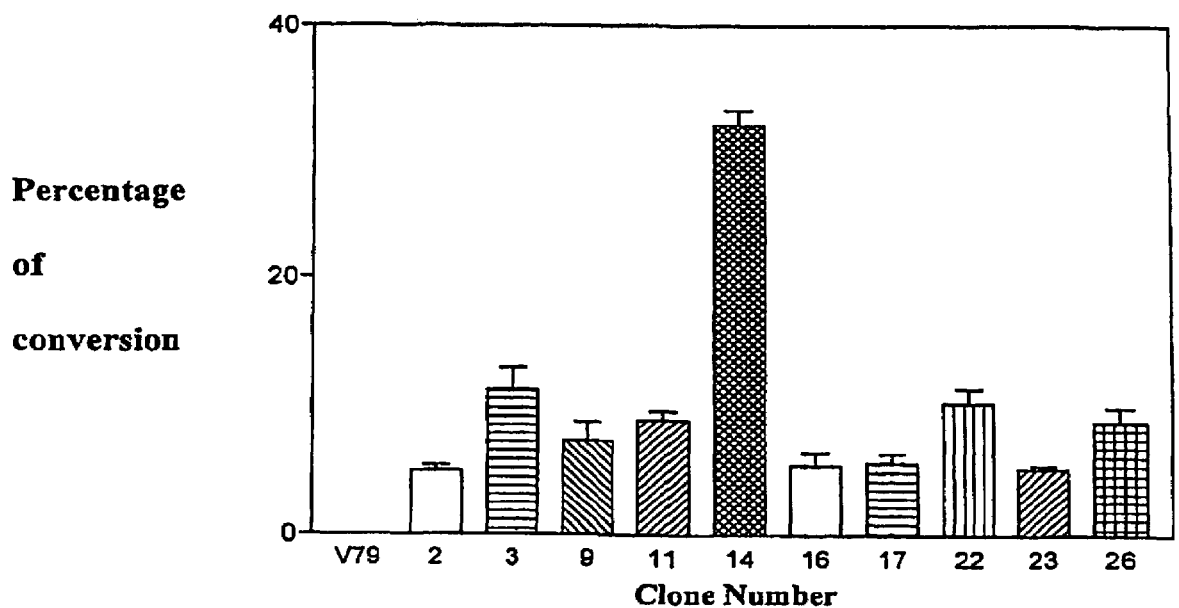
FIG. 5 Stability of CYP24/V79 cells in culture (one month).

FIG. 4 showed that CYP24 activity in clone No. 10, 13, and 21 was relatively low. The rest of the ten clones were maintained in culture for up to 3 month and CYP24 activity was checked every month. This time 500,000 cells of each clone were seeded in 6-well plate. The results in FIG. 5 showed that after one-month incubation, only clone No. 14 still has high CYP24 activity. The activity remains the same after 3 months.

Example 5

Functional Characterization of CYP24 Expressed in Hamster V79 Cells

Figure 6:
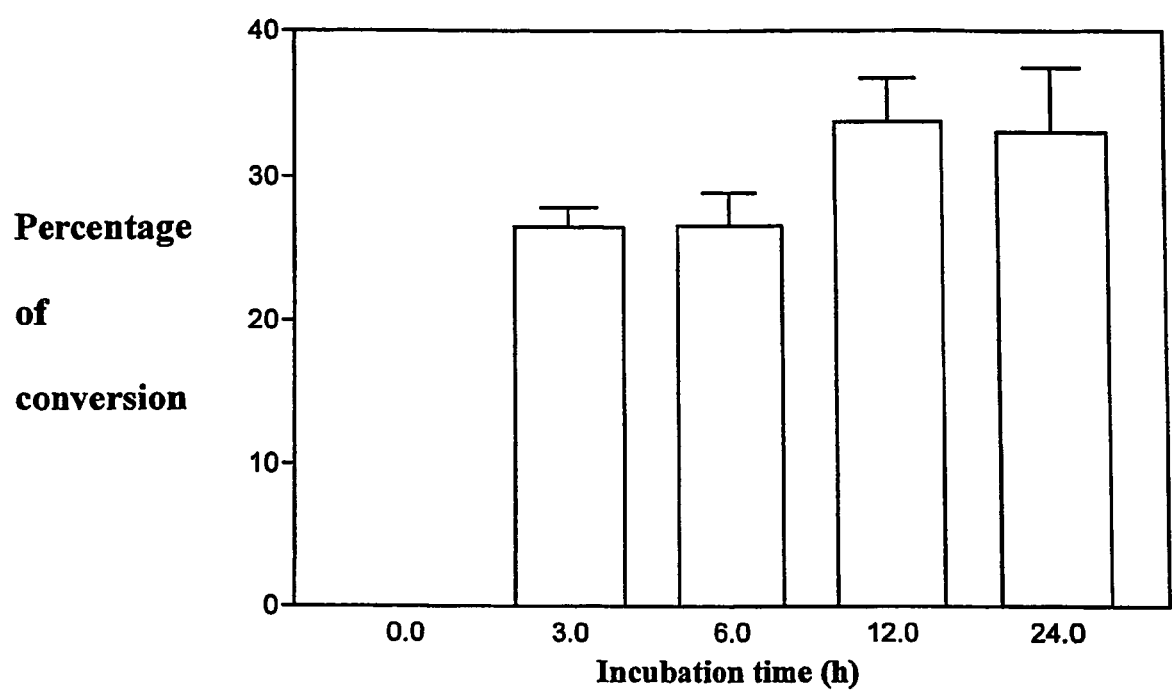
FIG. 6 Effect of incubation time on CYP24 activity.
Figure 7:
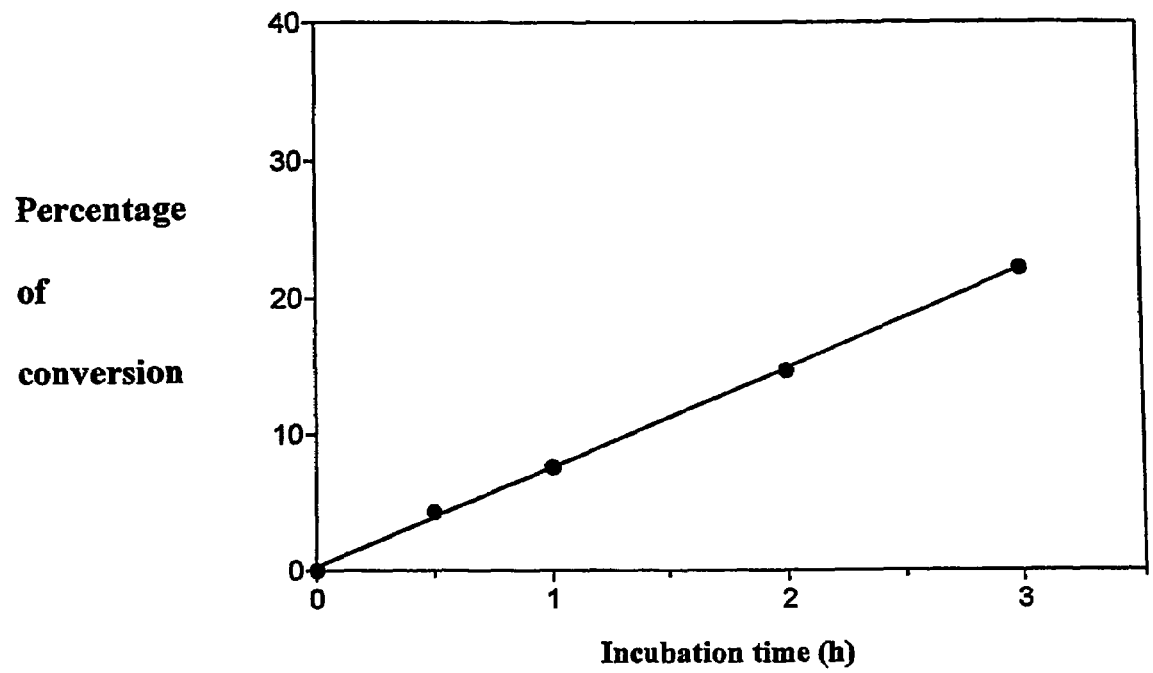
FIG. 7 Effect of incubation time on CYP24 activity.
Figure 8:
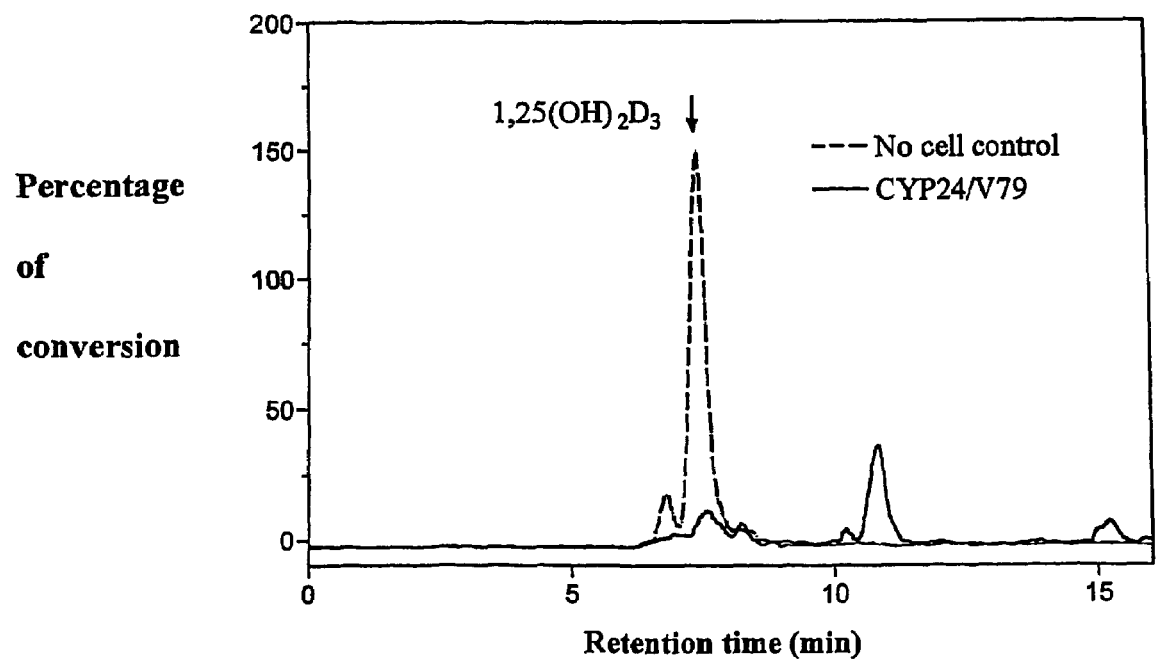
FIG. 8 $1,25(OH)_2D3$ metabolism by CYP24/V79 cells.

CYP24 activity in clone No. 14 was further characterized. First, a time course was carried out. CYP24/V79 cells were suspended, counted, and 500,000 cells were seeded in 6-well plate in 0.6 ml of medium containing 1.5 nM [$^3$H-1β]-1,25 (OH)$_2$D3. Cells were extracted at 0, 3, 6, 12, and 24 hours using Bligh-Dyer extraction method. The radioactivity present in aqueous phase was compared. FIG. 6 revealed that after 3 hours, the radioactivity in the aqueous is almost saturated. So another time course with shorter incubation time was carried out. Cells were extracted at 0, 0.5, 1, 2, and 3 hours and radioactivity present in aqueous phase compared. FIG. 7 showed that CYP24 activity in clone No. 14 is linear up to 3 hours. The organic phase from 3 hours was analyzed by HPLC and the results in FIG. 8 showed that the substrate was disappeared and a number of metabolites could be seen.

Example 6

HPLC Based Metabolic Comparison of CYP24 Expressing Cell Systems

Cell culture. V79-4, V79-CYP24 and HPK1A-ras cells were cultured in 150 mm tissue culture dishes with 25 ml of Dulbecco's Modified Eagle Medium (DMEM) supplemented with 10% (v/v) fetal bovine serum (FBS) and 5% (v/v) antibiotic/antimycotic in a humidified incubator at 37° C./5% CO$_2$. The media used for the V79-CYP24 cells was also supplemented with 0.4% (v/v) hygromycin B. subcultured into 6 well plates. After recovery, only the HPK1A-ras containing wells were treated with 10 nM 1α,25-(OH)$_2$D$_3$ for 18 hours.

Figure 9:
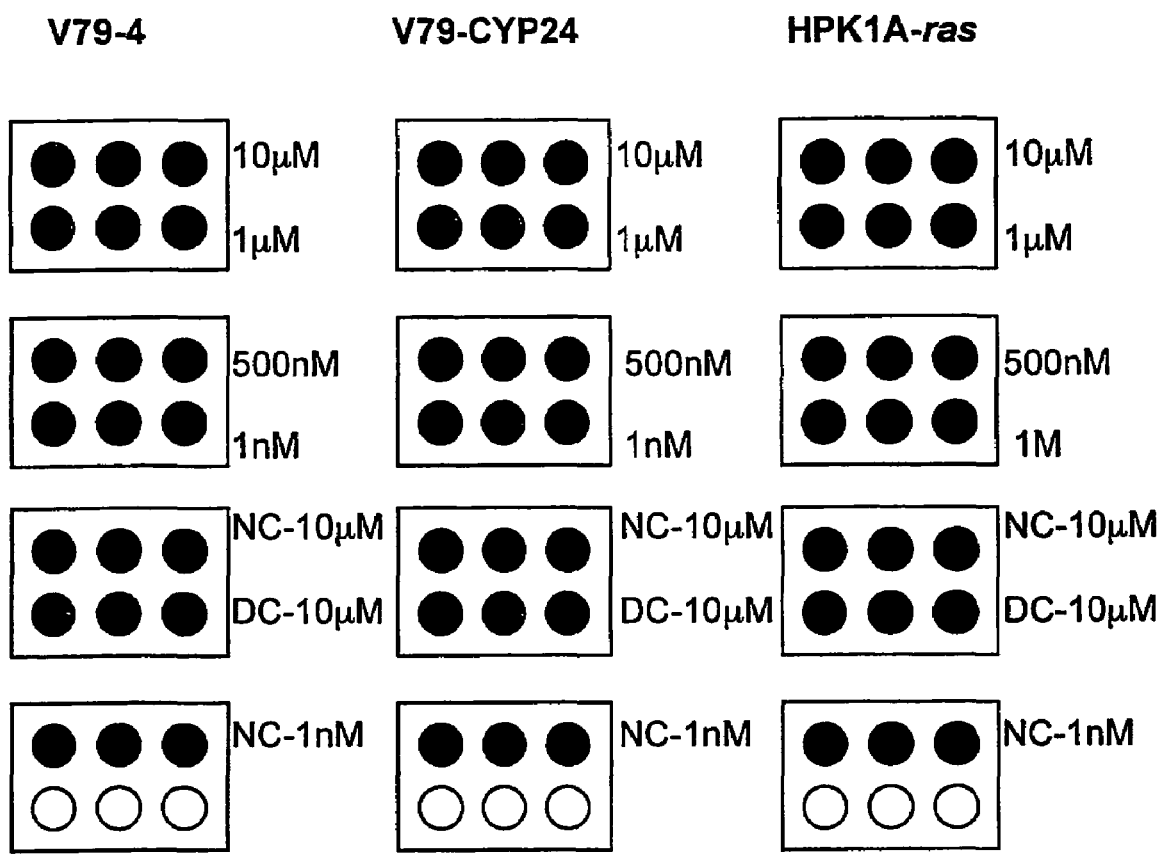
FIG. 9 Experimental controls of Example 6, which include wells containing dead cells (DC-10 μM) and wells without cells (NC-10 μM and 1 nM). V79-4, V79-CYP24 and HPK1A-ras cells were cultured.

Incubation with 1α,25-(OH)$_2$D$_3$. At approximately 80% confluence, V79-4, V79-CYP24 and HPK1A-ras cells were subcultured into 6 well plates. After recovery, only the HPK1A-ras containing wells were treated with 10 nM 1α,25-(OH)$_2$D$_3$ for 18 hours. At incubation time, the media was removed and the cells were rinsed with 2 ml of phosphate buffered saline (PBS). 2 ml of bovine serum albumin supplemented media (1% (w/v)) containing the appropriate amount of 1α,25-(OH)$_2$D$_3$ was introduced to the wells. Each well was supplemented with 2 μl of 100 mM 1,2-dianilinoethane (DPPD) antioxidant. Each cell line was incubated with 10 μM, 1 μM, 500 nM and 1 nM (150 000 CPM) 1α,25-(OH)$_2$D$_3$ or [1β-$^3$H] 1α,25-(OH)$_2$D$_3$ for 24 hours in triplicate wells. Experimental controls included wells containing dead cells (DC-10 μM) and wells without cells (NC-10 μM and 1 nM) according to the scheme in FIG. 9.

Total Lipid Extraction and High Performance Liquid Chromatgraphy. 1 μg of 1α—OH-D$_3$ was added to each well as an internal recovery standard. Media and cells were extracted according to a method modified from that of Bligh and Dyer (Bligh, E., Dyer, W. Can. J. Biochem. 37: 911-917. 1959). The aqueous phase was re-extracted with 5 ml methylene chloride in the presence of 0.01% (v/v) glacial acetic acid in order to isolate the water soluble catabolites. The organic phase was subjected to normal phase HPLC using a solvent system of 91/7/2-hexane/isopropanol/methanol (percentage of total flow) at a flow rate of 1 ml/minute on Zorbax-SIL (3μ) [Agilent]. The aqueous phase re-extract was subjected to reversed phase HPLC using an acetonitrile/water based gradient system over 30 minutes in the presence of 0.1% (percentage of total flow) glacial acetic acid. A flow rate of 1 ml/minute was used on Zorbax SB-C18 (3.5μ) [Agilent]. Metabolite quantitation was facilitated by diode array detection (UV$_{265}$). Metabolite identification was based on observation of the characteristic vitamin D chromophore ($\lambda_{max}=265$; $\epsilon=18\ 300$) and on co-chromatography with authentic synthesized standards. On-line radioflow chromatography of the samples incubated with [1β-$^3$H] 1α,25-(OH)$_2$D$_3$ also facilitated metabolite identity, and subsequent MS analyses are expected to confirm these observations.

Figure 10A:
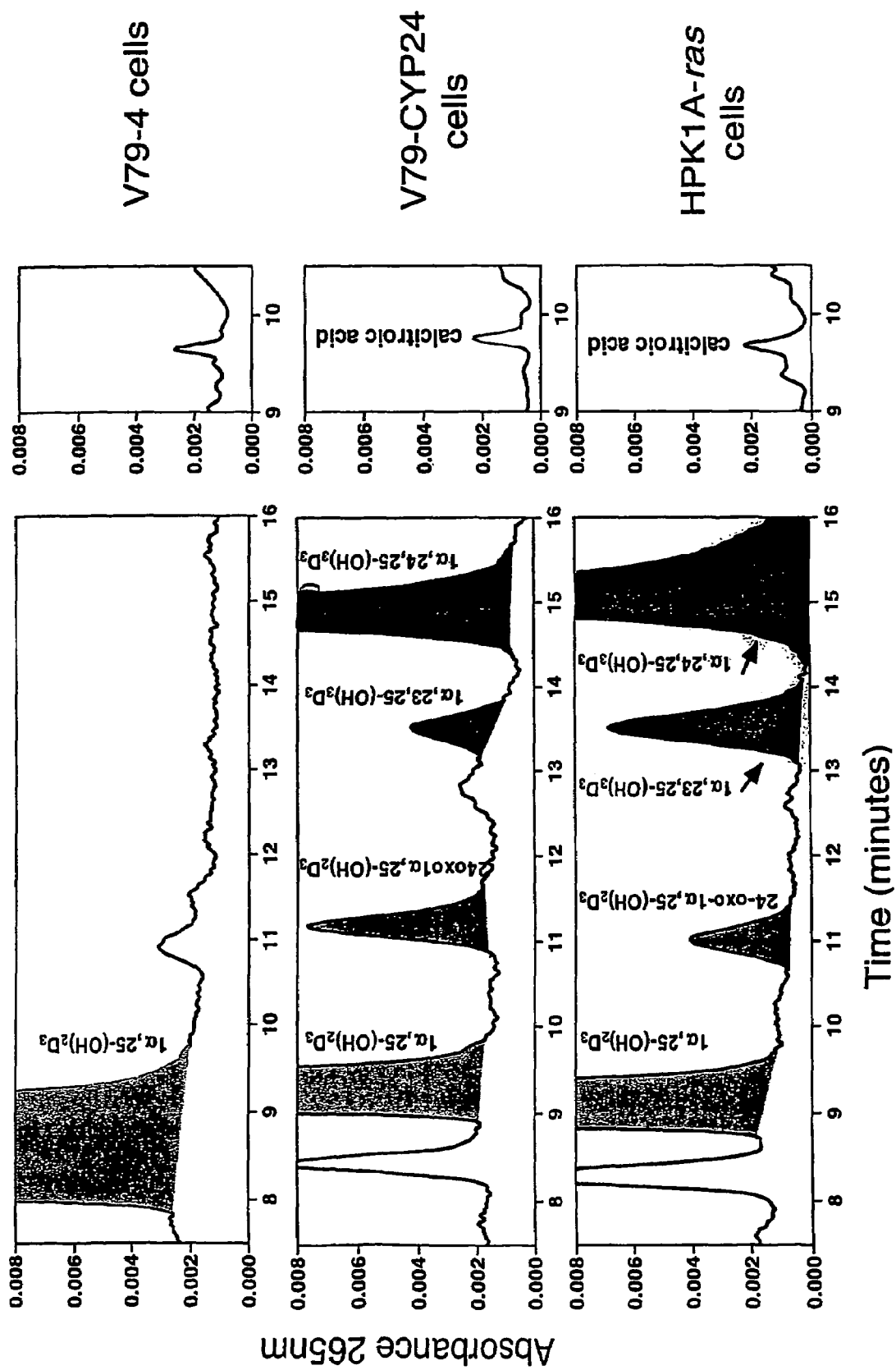
FIG. 10A Metabolism of 10 μM $1\alpha,25$-$(OH)_2D_3$: organic and aqueous phases.
Figure 10B:
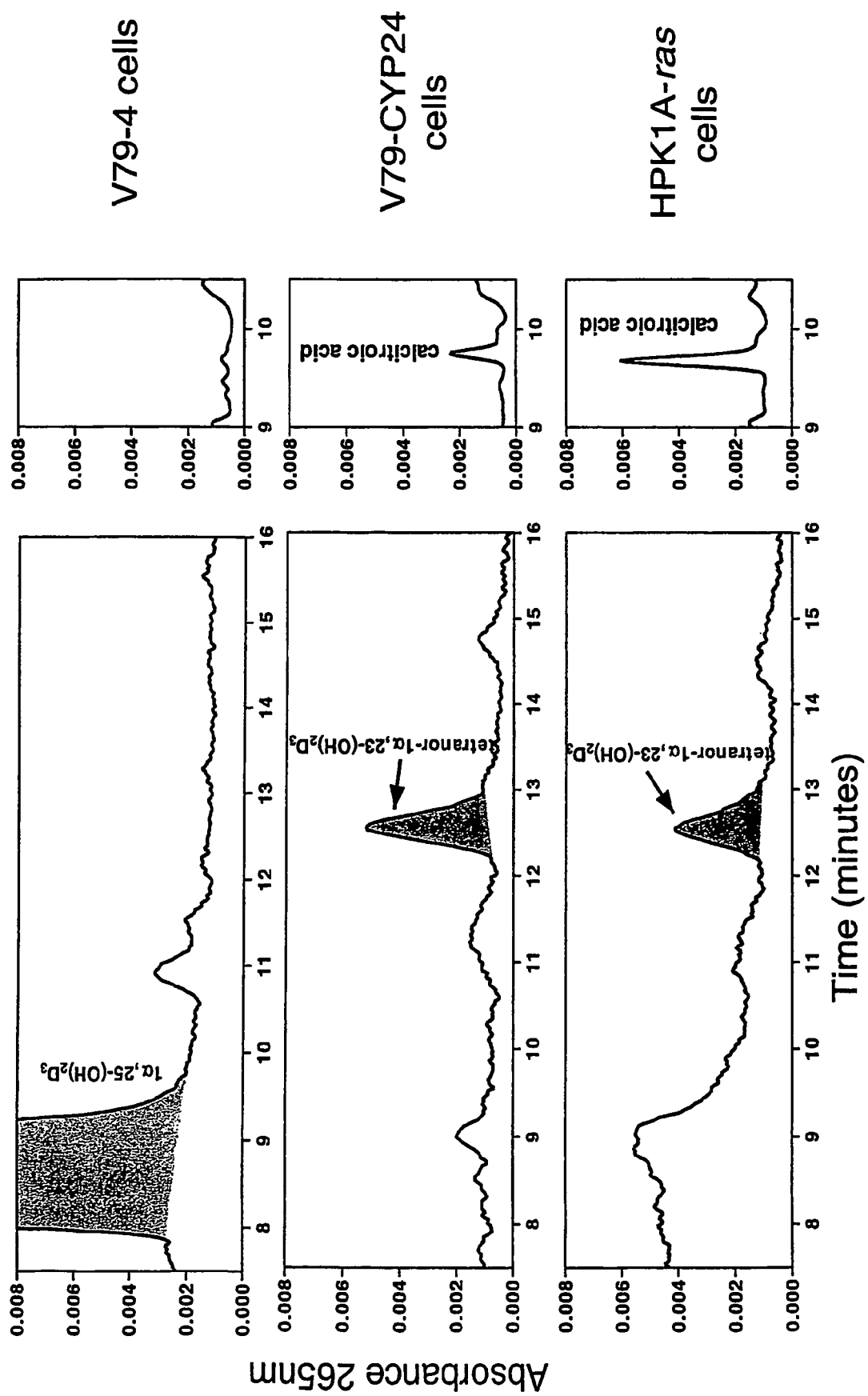
FIG. 10B Metabolism of 500 nM $1\alpha,25$-$(OH)_2D_3$: organic and aqueous phases.

The stable transfected cell line V79-CYP24 was shown to possess similar capacity to metabolize 1α,25-(OH)$_2$D$_3$ via the intermediates of C24-oxidation to calcitroic acid when compared to a previously well-studied CYP24 expressing system, the human keratinocyte cell line, HPK1A-ras. Metabolism was assessed based on substrate disappearance and total product formation. Conversely, the un-transfected V79-4 cells showed no metabolism. Substrate concentration dependent patterns of metabolite production are conserved between the two systems, such that at high concentrations (10 μM) the proximal pathway intermediates predominated, whereas at the low concentrations, the more polar metabolites were the most prevalent (1-500 nM) (FIGS. 10A and 10B) (Kaufmann, M., Masuda. S., and Jones, G. 2001. 23$^{rd}$ Annual Meeting of the American Society for Bone and Mineral Research, Phoenix, Ariz., USA. Oct. 12-16, 2001. J. Bone Miner. Res. 16:Supp. 1. Abstract SA529. Poster Presentation. These observations confirm that the metabolites previously observed in other vitamin D target cell systems, are due to CYP24 catalyzed catabolism.

Example 7

Identification of Modulators of CYP24

Figure 11:
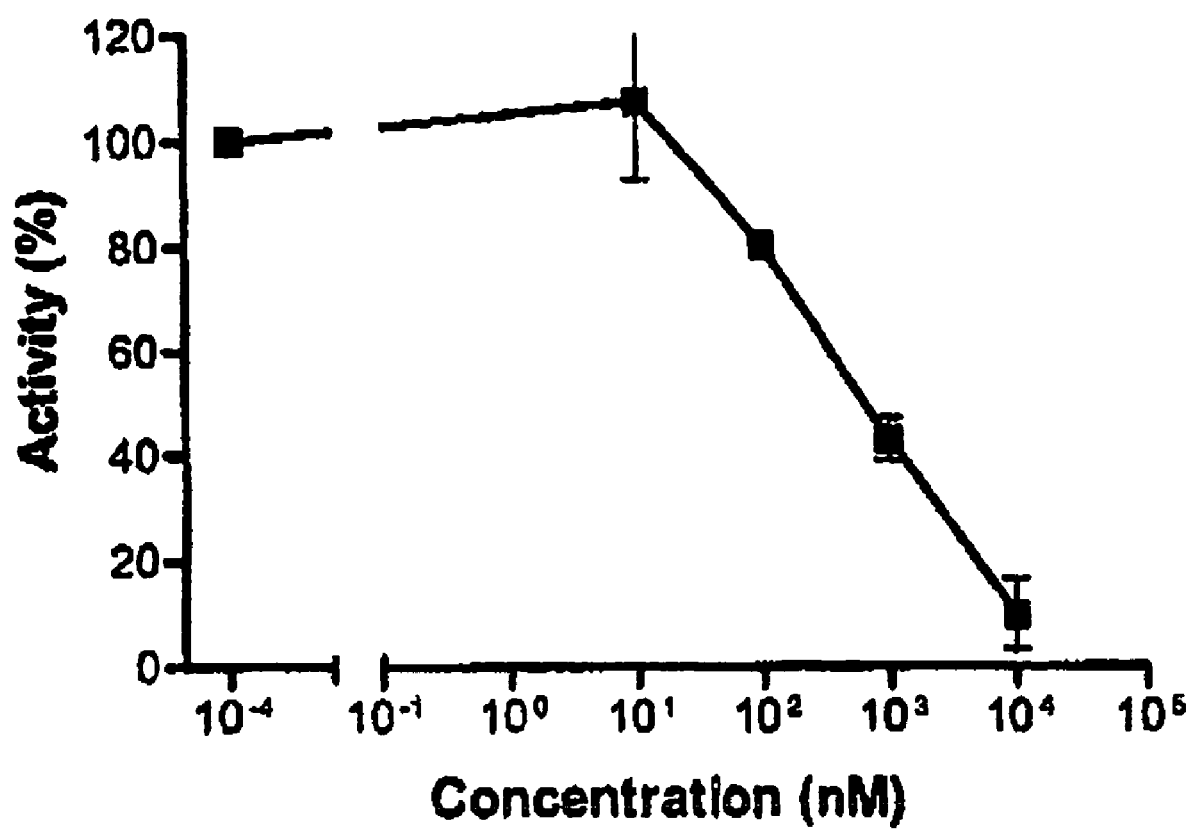
FIG. 11 Inhibition of Ketoconazole (CYP24 stable transfected cell lines).

Ketoconazole(cis-1-acetyl-4-[4-[[2-(2,4-dichlorophenyl)-2-(1H-imidazol-1-ylmethyl)-1,3-dioxolan-4-yl]methoxyl]phenyl]piperazine) was administered to CYP24/V79 cells. CYP24/V79 cells were suspended, counted, seeded on well plates and extracted using the Bligh-Dyer extraction method. The organic phase from 3 hours was analyzed by HPLC and the results showed that activity of CYP24 decreased (FIG. 11). Since ketoconazole reduced CYP24 activity, these results show that ketoconazole is an inhibitor of the polypeptide. The protocol used in the ketoconazole experiment is shown below. This protocol can be used to screen for other modulators of CYP24.

Other candidate compounds were screened using the same method and are used to identify both activators and inhibitors of CYP24. Other inhibitors, for example, include erythromycin and itraconazole. The activators and inhibitors are useful in vitro and in vivo.

Example 8

CYP24 Enzyme Assay Using Stable CYP24-V79 Cells— (Inhibition by Ketoconazole or Modulation by Other Test Compounds)

CYP24-V79 cells and HPK1A-ras cells were subcultured. For example, 2 million CYP24-V79 cells were optionally subcultured in 1* 150 mm plate two days before the assay. HPK1A-ras cells were preferably induced, for example, 18 hours prior to the start of the assay. To induce cells, media was removed and the cells washed with 1× PBS buffer. About 16-18 mL of fresh media was added to each large plate and 16-18 ml of $10^{-5}$ M 1,25(OH)$_2$D$_3$ (i.e. 1 mL of $10^{-5}$ M 1,25(OH)$_2$D$_3$ per 1 mL media ($10^{-8}$ M final concentration)).

Next, a cell suspension was prepared at the day of assay by removing the medium and washing the cell with PBS. 2 ml tripsin/EDTA was added to the plate which was kept in 37° C. for 5 min. Next, 3 ml EDTA medium+1% FCS was added followed by transfer to a 50 ml tube. The plate was washed with 5 ml PBS and mixed. The mix was centrifuged (2,000 rpm, 5 min) and the suspended cells pelleted in DMEM medium+1% BSA.

In one embodiment, since the V79-CYP24 cells lift quickly they were held at 37° C. for about 2 minutes but the HPK1A-ras cells were left for approximately 10 minutes. About 5 mL 1× PBS buffer was added to collect cells from the plate and then placed in a 50 mL tube followed by repetition with second cell line. About 5 mL 1× PBS buffer was added to further wash the plate and added to the original 50 mL tube. Tubes were centrifuged (2,000 rpm/800 g for 6 minutes) and the supernatant removed. The pellet was resuspended in DMEM+1% BSA media (initial resuspension volume will depend on assay requirements, i.e. if require 12 mL for assay, start there). The cells were counted via hemocytometer and density adjusted to 250,000 cells/ 150 μL (1.67 million/1 mL) and then 150 μL added to appropriately labeled wells of 48-well plate. Cells had about 30 minutes in the incubator to adhere to the wells. The cells were counted and cell density was adjusted to 500,000/150 μL. Then the 150 μL cell suspension was added to each well in a 48-well plate (including 3 well as no cell control (NCC)), and a 3 well cells without drug or inhibitor as control). For example:

| NCC | NCC | NCC | No T | No T | No T |
|-----|-----|-----|------|------|------|
| K-8 | K-8 | K-8 | K-7  | K-7  | K-7  |
| K-6 | K-6 | K-6 | K-5  | K-5  | K-5  |

About 25 μL medium was added containing ketoconazole (examples of final concentrations include $10^{-5}$ M, $10^{-6}$ M, $10^{-7}$ M, $10^{-8}$ M or $5 \times 10^{-7}$, $5 \times 10^{-8}$, or $5 \times 10^{-9}$). The IC$_{50}$ for ketoconazole is around $5 \times 10^{-7}$ M. The plate was kept in 37° C. for 10 min.

Other test compounds (inhibitor or activator) were used at a series of variable concentrations such as $10^{-6}$, $10^{-7}$, $10^{-8}$, $10^{-9}$ or $10^{-10}$ or $5 \times 10^{-7}$, $5 \times 10^{-8}$, or $5 \times 10^{-9}$.

Substrate was prepared with a predetermined amount of DMEM+1% BSA medium (25*well number+200) μL in a tube, followed by adding an amount of $^3$H-1,25(OH)$_2$D$_3$ (well number+2) μL and a certain amount of 100 mM DPPD (well number/5) μL and mixing them by vortex.

| | |
|---|---|
| DMEM + 1% BSA | 550 μL |
| DPPD | 4.4 μL |
| $^3$H-1 α, 25(OH)$_2$D$_3$ (50,000 CPM/μL) mix | 11 μL |

To incubate the samples, 25 μL substrate was added to each well and the plate was incubated at 37° C. for 2 hour. 25 μL substrate was added to the counting plate (2 wells) as a total count.

In the assay, wells (optionally eight wells) remained untreated with inhibitor to provide controls. Substrate was added to four of these wells (100% cell control). To the remaining four wells, nothing was added until after the reaction was stopped with the first addition of methanol. At this point, 25 mL of the substrate solution (0% cell control) was added. Some substrate solution was set aside, and 25 mL added directly to scintillation fluid when counting.

Lipid extraction (Bligh-Dyer) and counting were done by adding 500 μL methanol to each well to stop the reaction, followed by transfer to a tube. Next, 250 μL dichloromethane was added followed by vortexing. An additional 250 μL dichloromethane was added along with 250 μL saturated KCl. The mix was centrifuged at 4000 rpm for 5 min. About 100 μL of aqueous phase (upper phase) was transferred to a plastic counting plate with 600 μL of scintillation fluid was added to each well. The plate is counted in a scintillation counter. Enzyme activity was then calculated. CPM of cell control after subtraction of CPM of NCC is as 100% enzyme activity.

References for the above protocol include:

Ray S, Ray R, Holick M. Metabolism of $^3$H-1alpha, 25-dihydroxyvitamin D$_3$ in the cultured human keratinocytes (1995) 59:117-122

Dilworth F J, Scott I, Green A, Strugnell S, Guo Y D, Roberts E A, Kremer R, Calverley, M J, Makin H L J, Jones G. Different mechanisms of hydroxylation site selection by liver and kidney cytochrome P450 species (CYP27 and CYP24) involved in Vitamin D metabolism. (1995) J Biochem 270(28):16766-16774

In another example, Vitamin D analog candidate inhibitor compounds, called I(a) through I(k) were tested as follows.

Dilution of test compounds
Stock $10^{-3}$ M

| Concentration (final) | From previous step | (μL) DMEM + 1% BSA | (μL) Concentration (actual) |
|---|---|---|---|
| 10-5 M | 10 | 115 | 8 * 10-5 M |
| 10-6 M | 12.5 | 112.5 | 8 * 10-6 M |
| 10-7 M | 12.5 | 112.5 | 8 * 10-7 M |
| 10-8 M | 12.5 | 112.5 | 8 * 10-8 M |

Figure 14:
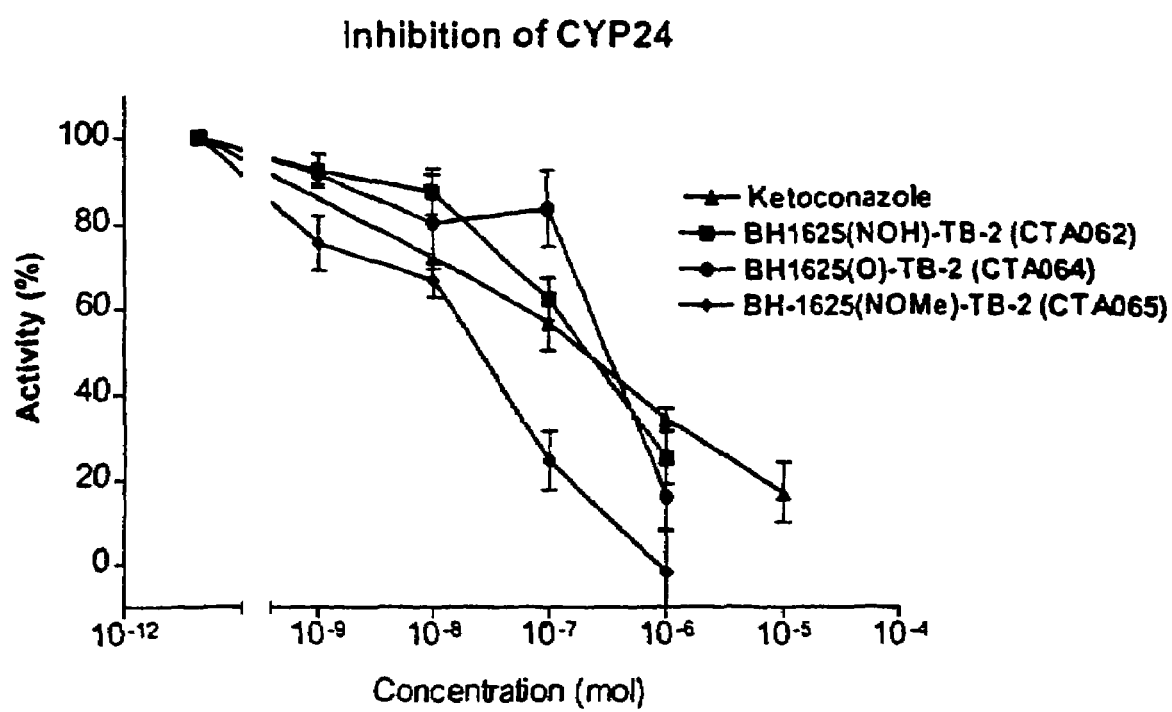
FIG. 14. Graph showing inhibition of CYP24 activity by candidate compounds.

Compounds of Formula I(a), I(c), I(e), I(g), I(i) and I(k) showed significantly greater inhibition of CYP24 than ketoconazole. A graph showing inhibition of CYP24 activity by compounds I(a) and I(c) (indicated as BH1625(NOH)-TB-2 (CTA062) and BH-1625(NOMe)-TB-2-(CTA065) respectively) compared to ketoconazole is shown in FIG. 14.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications, including Genbank database entries, are herein incorporated by reference in their entirety to the same extent as if each individual publication, patent or patent application was specifically and individually indicated to be incorporated by reference in its entirety.

We claim:

1. A cell line that stably expresses an active CYP24 polypeptide, comprising a recombinant CYP24 nucleic acid molecule that is operably linked to a promoter to enable expression thereof, wherein the recombinant CYP24 nucleic acid molecule comprises a nucleic acid having at least 98% identity to SEQ ID NO: 1 that encodes the active CYP24 polypeptide that catalyzes hydroxylation of Vitamin D metabolites.

2. The cell line of claim 1, wherein the cell is a mammalian cell or an insect cell.

3. The cell line of claim 1, wherein the cell line expresses adrenodoxin (ADX) and adrenodoxin reductase (ADR).

4. The cell line of claim 1, wherein the cell is a V79 cell or a Sf9 cell.

5. The cell line of claim 1, wherein the CYP24 nucleic acid is HPK-1A ras cell CYP24 as shown in SEQ ID NO: 1.

6. The cell line of claim 1 wherein the recombinant CYP24 nucleic acid molecule is in a vector comprising the CYP24 nucleic acid molecule.

7. The cell line of claim 6 wherein the vector is pFast-Bac1, pcDNA3.1 or pcDNA3.1-Hygro(+).

8. A cell culture that stably expresses CYP24 polypeptide comprising cells of the cell line of claim 1.

9. A cell culture comprising cells that stably express active CYP24 polypeptide, the cells comprising a recombinant CYP24 nucleic acid molecule that is operably linked to a promoter to enable expression thereof, in a medium capable of sustaining growth and replication of the cells, wherein the recombinant CYP24 nucleic acid molecule comprises a nucleic acid having at least 98% identity to SEQ ID NO: 1 that encodes the active CYP24 polypeptide that catalyzes hydroxylation of Vitamin D metabolites.

10. The cell culture of claim 9, wherein the cells further comprise an antibiotic resistance gene and the cell culture includes an antibiotic encoded by the antibiotic resistance gene.

* * * * *

SEQUENCE LISTING

<160> NUMBER OF SEQ ID NOS: 10

<210> SEQ ID NO 1
<211> LENGTH: 1560
<212> TYPE: DNA
<213> ORGANISM: Homo sapiens with NheI site at 5' end and XhoI site at
      3' end

<400> SEQUENCE: 1

```
gctagcacca tgagctcccc catcagcaag agccgctcgc ttgccgcctt cctgcagcag     60
ctgcgcagtc cgaggcagcc cccgagactg gtgacatcta cggcgtacac gtcccctcag    120
ccgcgagagg tgccagtctg cccgctgaca gctggtggcg agactcagaa cgcggccgcc    180
ctgccgggcc ccaccagctg gccactgctg ggcagcctgc tgcagattct ctggaagggg    240
ggtctcaaga acagcacga caccctggtg gagtaccaca agaagtatgg caagattttc    300
cgcatgaagt tgggttcctt tgagtcggtg cacctgggct cgccatgcct gctggaagcg    360
ctgtaccgca ccgagagcgc gtacccgcag cggctggaga tcaaaccgtg gaaggcctat    420
cgcgactacc gcaaagaagg ctacgggctg ctgatcctgg aaggggaaga ctggcagcgg    480
gtccggagtg cctttcaaaa gaaactaatg aaaccagggg aagtgatgaa gctggacaac    540
aaaatcaatg aggtcttggc cgattttatg ggcagaatag atgagctctg tgatgaaaga    600
ggccacgttg aagacttgta cagcgaactg aacaaatggt cgtttgaaag tatctgcctc    660
gtgttgtatg agaagagatt tgggcttctc cagaagaatg caggggatga agctgtgaac    720
ttcatcatgg ccatcaaaac aatgatgagc acgtttggga ggatgatggt cactccagtc    780
gagctgcaca gagcctcaa caccaaggtc tggcaggacc acactctggc ctgggacacc    840
attttcaaat cagtcaaagc ttgtatcgac aaccggttag agaagtattc tcagcagcct    900
agtgcagatt ccctttgtga catttatcac cagaatcggc tttcaaagaa agaattgtat    960
gctgctgtca cagagctcca gctggctgcg gtggaaacga cagcaaacag tctaatgtgg   1020
attctctaca atttatcccg taatccccaa gtgcaacaaa agcttcttaa ggaaattcaa   1080
agtgtattac ctgagaatca ggtgccacgg gcagaagatt tgaggaatat gccgtattta   1140
aaagcctgtc tgaaagaatc tatgaggctt acgccgagtg taccatttac aactcggact   1200
cttgacaagg caacagttct gggtgaatat gctttaccca aggaacagt gctcatgcta   1260
aatacccagg tgttgggatc cagtgaagac aattttgaag attcaagtca gtttagacct   1320
gaacgttggc ttcaggagaa ggaaaaaatt aatccttttg cgcatcttcc atttggcgtt   1380
ggaaaaagaa tgtgcattgg tcgccgatta gcagagcttc aactgcattt ggctcttttgt   1440
tggattgtcc gcaaatacga catccaggcc acagacaatg agcctgttga gatgctacac   1500
tcaggcaccc tggtgcccag ccgggaactc cccatcgcgt tttgccagcg ataactcgag   1560
```

<210> SEQ ID NO 2
<211> LENGTH: 514
<212> TYPE: PRT
<213> ORGANISM: Homo sapiens

<400> SEQUENCE: 2

```
Met Ser Ser Pro Ile Ser Lys Ser Arg Ser Leu Ala Ala Phe Leu Gln
1               5                   10                  15

Gln Leu Arg Ser Pro Arg Gln Pro Pro Arg Leu Val Thr Ser Thr Ala
            20                  25                  30
```

-continued

```
Tyr Thr Ser Pro Gln Pro Arg Glu Val Pro Val Cys Pro Leu Thr Ala
         35                  40                  45

Gly Gly Glu Thr Gln Asn Ala Ala Leu Pro Gly Pro Thr Ser Trp
 50                  55                  60

Pro Leu Leu Gly Ser Leu Leu Gln Ile Leu Trp Lys Gly Gly Leu Lys
 65                  70                  75                  80

Lys Gln His Asp Thr Leu Val Glu Tyr His Lys Lys Tyr Gly Lys Ile
                 85                  90                  95

Phe Arg Met Lys Leu Gly Ser Phe Glu Ser Val His Leu Gly Ser Pro
            100                 105                 110

Cys Leu Leu Glu Ala Leu Tyr Arg Thr Glu Ser Ala Tyr Pro Gln Arg
            115                 120                 125

Leu Glu Ile Lys Pro Trp Lys Ala Tyr Arg Asp Tyr Arg Lys Glu Gly
    130                 135                 140

Tyr Gly Leu Leu Ile Leu Glu Gly Glu Asp Trp Gln Arg Val Arg Ser
145                 150                 155                 160

Ala Phe Gln Lys Lys Leu Met Lys Pro Gly Glu Val Met Lys Leu Asp
                165                 170                 175

Asn Lys Ile Asn Glu Val Leu Ala Asp Phe Met Gly Arg Ile Asp Glu
            180                 185                 190

Leu Cys Asp Glu Arg Gly His Val Glu Asp Leu Tyr Ser Glu Leu Asn
            195                 200                 205

Lys Trp Ser Phe Glu Ser Ile Cys Leu Val Leu Tyr Glu Lys Arg Phe
    210                 215                 220

Gly Leu Leu Gln Lys Asn Ala Gly Asp Glu Ala Val Asn Phe Ile Met
225                 230                 235                 240

Ala Ile Lys Thr Met Met Ser Thr Phe Gly Arg Met Met Val Thr Pro
                245                 250                 255

Val Glu Leu His Lys Ser Leu Asn Thr Lys Val Trp Gln Asp His Thr
            260                 265                 270

Leu Ala Trp Asp Thr Ile Phe Lys Ser Val Lys Ala Cys Ile Asp Asn
    275                 280                 285

Arg Leu Glu Lys Tyr Ser Gln Pro Ser Ala Asp Phe Leu Cys Asp
    290                 295                 300

Ile Tyr His Gln Asn Arg Leu Ser Lys Lys Glu Leu Tyr Ala Ala Val
305                 310                 315                 320

Thr Glu Leu Gln Leu Ala Ala Val Glu Thr Thr Ala Asn Ser Leu Met
                325                 330                 335

Trp Ile Leu Tyr Asn Leu Ser Arg Asn Pro Gln Val Gln Gln Lys Leu
            340                 345                 350

Leu Lys Glu Ile Gln Ser Val Leu Pro Glu Asn Gln Val Pro Arg Ala
    355                 360                 365

Glu Asp Leu Arg Asn Met Pro Tyr Leu Lys Ala Cys Leu Lys Glu Ser
    370                 375                 380

Met Arg Leu Thr Pro Ser Val Pro Phe Thr Thr Arg Thr Leu Asp Lys
385                 390                 395                 400

Ala Thr Val Leu Gly Glu Tyr Ala Leu Pro Lys Gly Thr Val Leu Met
                405                 410                 415

Leu Asn Thr Gln Val Leu Gly Ser Ser Glu Asp Asn Phe Glu Asp Ser
            420                 425                 430

Ser Gln Phe Arg Pro Glu Arg Trp Leu Gln Glu Lys Glu Lys Ile Asn
            435                 440                 445

Pro Phe Ala His Leu Pro Phe Gly Val Gly Lys Arg Met Cys Ile Gly
```

```
              450                455                460
Arg Arg Leu Ala Glu Leu Gln Leu His Leu Ala Leu Cys Trp Ile Val
465                470                475                480

Arg Lys Tyr Asp Ile Gln Ala Thr Asp Asn Glu Pro Val Glu Met Leu
                485                490                495

His Ser Gly Thr Leu Val Pro Ser Arg Glu Leu Pro Ile Ala Phe Cys
                500                505                510

Gln Arg

<210> SEQ ID NO 3
<211> LENGTH: 3274
<212> TYPE: DNA
<213> ORGANISM: Homo sapiens

<400> SEQUENCE: 3
tggagaggga caggaggaaa cgcagcgcca gcagcatctc atctaccctc cttgacacct      60
ccccgtggct ccagccagac cctagaggtc agccttgcgg accaacagga ggactcccag     120
cttttccttt tcaagaggtc cccagacacc ggccaccctc ttccagcccc tgcggccagt     180
gcaaggaggc accaatgctc tgaggctgtc gcgtggtgca gcgtcgagca tcctcgccga     240
ggtcctttct gctgcctgtc ccgcctcacc ccgctccatc acaccagctg gccctctttg     300
cttccttttc ccagaatcgt taagcccga ctcccactag cacctcgtac caacctcgcc      360 ccacccatc ctcctgcctt cccgcgctcc ggtgtccccc gctgccatga gctcccccat      420
cagcaagagc cgctcgcttg ccgccttcct gcagcagctg cgcagtccga ggcagccccc     480
gagactggtg acatctacgg cgtacacgtc ccctcagccg cgagaggtgc cagtctgccc     540
gctgacagct ggtggcgaga ctcagaacgc ggccgccctg ccgggcccca ccagctggcc     600
actgctgggc agcctgctgc agattctctg gaagggggt ctcaagaaac agcacgacac      660
cctggtggag taccacaaga agtatggcaa gattttccgc atgaagttgg gttcctttga     720
gtcggtgcac ctgggctcgc catgcctgct ggaagcgctg taccgcaccg agagcgcgta     780
cccgcagcgg ctggagatca aaccgtggaa ggcctatcgc gactaccgca agaaggcta     840 cgggctgctg atcctggaag ggaagactg gcagcgggtc cggagtgcct ttcaaaagaa      900
actaatgaaa ccaggggaag tgatgaagct ggacaacaaa atcaatgagg tcttggccga     960
ttttatgggc agaatagatg agctctgtga tgaaagaggc cacgttgaag acttgtacag    1020
cgaactgaac aaatggtcgt ttgaaagtat ctgcctcgtg ttgtatgaga agagatttgg    1080
gcttctccag aagaatgcag gggatgaagc tgtgaacttc atcatggcca tcaaaacaat    1140
gatgagcacg tttgggagga tgatggtcac tccagtcgag ctgcacaaga gcctcaacac    1200
caaggtctgg caggaccaca ctctggcctg ggacaccatt tcaaatcag tcaaagcttg     1260 tatcgacaac cggttagaga agtattctca gcagcctagt gcagatttcc tttgtgacat    1320
ttatcaccag aatcggcttt caagaaaga attgtatgct gctgtcacag agctccagct    1380
ggctgcggtg gaaacgacag caaacagtct aatgtggatt ctctacaatt tatcccgtaa    1440
tccccaagtg caacaaaagc ttcttaagga aattcaaagt gtattacctg agaatcaggt    1500
gccacgggca agagattga ggaatatgcc gtatttaaaa gcctgtctga agaatctat      1560 gaggcttacg ccgagtgtac catttacaac tcggactctt gacaaggcaa cagttctggg    1620
tgaatatgct ttaccaaag gaacagtgct catgctaaat acccaggtgt tgggatccag    1680
tgaagacaat tttgaagatt caagtcagtt tagacctgaa cgttggcttc aggagaagga    1740
```

```
aaaaattaat ccttttgcgc atcttccatt tggcgttgga aaaagaatgt gcattggtcg    1800
ccgattagca gagcttcaac tgcatttggc tctttgttgg attgtccgca aatacgacat    1860
ccaggccaca gacaatgagc tgttgagat gctacactca ggcaccctgg tgcccagccg     1920
ggaactcccc atcgcgtttt gccagcgata atacgcctca gatggtggta tttgctaaca    1980
tcatatccaa ctcagggaag cggactgagt gctgggatcc aaggcattct acagggttca    2040
ctgctggttt acacttcacc tgtgtcagca ccatcttcag gtgcttagaa tggcctggga    2100
gcctgttctg tcttgcatct tccatgacat gaaagggagg ctggcacttg tcagtcaggt    2160
agaggttaca aaccgtttca ggccctgcct accacattca ctgtttgaat ctttaattcc    2220
caagaataag tttacatttc acaatgaatg acctacaaca gctaaatttt ctggggctgg    2280
gagtaatact gacaatccat ttactgtagc tctgcttaat gtactactta ggaaaatgtc    2340
cctgcttaat aatgtaagcc aagctaaatg atggttaaag ttatcaggcc tcccatgaaa    2400
ttgcgttctt cctgcattga aataaaaaca ttattgggaa actagagaac acctctattt    2460
ttaaaaggac tttaacgaag tcaaacaact tataagacta gtgattcact ggggcattat    2520
tttgttagag gaccttaaaa ttgtttattt tttaaatgtg attcctttat ggcattaggg    2580
taaagatgaa gcaataattt ttaaattgtg tatgtgcata tgaagcacag acatgcatgt    2640
gtgtgtgtgt ctgtgtgtgt gtgtccgtgt atgtgtgtgt gggttctaat ggtaatttgc    2700
ctcagtcatt tttttaatat ttgcagtact tgatttagga tctgtggtgc agggcaatgt    2760
ttcaaagttt agtcacagct taaaaacatt cagtgtgact ttaatattat aaaatgattt    2820
cccatgccat aatttttctg tctattaaat gggacaagtg taaagcatgc aaaagttaga    2880
gatctgttat ataacatttg ttttgtgatt tgaactccta ggaaaaatat gatttcataa    2940
atgtaaaatg cacagaaatg catgcaatac ttataagact taaaaattgt gtttacagat    3000
ggtttatttg tgcatatttt tactactgct tttcctaaat gcatactgta tataattctg    3060
tgtatttgat aaatatttct tcctacatta tattttaga atatttcaga aatatacatt     3120 tatgtctttta tattgtaata aatatgtaca tatctaggta tatgctttct ctctgctgtg   3180
aaattatttt tagaattata aattcacgtc ttgtcagatt tcatctgtat accttcaaat    3240
tctctgaaag taaaaataaa agttttaaa tatt                                 3274
```

<210> SEQ ID NO 4
<211> LENGTH: 32
<212> TYPE: DNA
<213> ORGANISM: Artificial Sequence
<220> FEATURE:
<223> OTHER INFORMATION: Forward primer for CYP24 RT-PCR with NheI site

<400> SEQUENCE: 4
tacgctagca ccatgagctc ccccatcagc aa                                  32

<210> SEQ ID NO 5
<211> LENGTH: 32
<212> TYPE: DNA
<213> ORGANISM: Artificial Sequence
<220> FEATURE:
<223> OTHER INFORMATION: Reverse primer for CYP24 RT PCR with XhoI site

<400> SEQUENCE: 5
aggctcgagt tatcgctggc aaaacgcgat gg                                  32

<210> SEQ ID NO 6
<211> LENGTH: 22

```
<212> TYPE: DNA
<213> ORGANISM: Artificial Sequence
<220> FEATURE:
<223> OTHER INFORMATION: Forward primer used to generate his-tagged
      version of CYP24

<400> SEQUENCE: 6
cccaaaggaa cagtgctcat gc                                              22

<210> SEQ ID NO 7
<211> LENGTH: 31
<212> TYPE: DNA
<213> ORGANISM: Artificial Sequence
<220> FEATURE:
<223> OTHER INFORMATION: Reverse primer used to generate his-tagged
      version of CYP24

<400> SEQUENCE: 7
tggctcgagt cgctggcaaa acgcgatggg g                                    31

<210> SEQ ID NO 8
<211> LENGTH: 8
<212> TYPE: PRT
<213> ORGANISM: Artificial Sequence
<220> FEATURE:
<223> OTHER INFORMATION: His-tag sequence inserted to C-terminus of
      CYP24

<400> SEQUENCE: 8

Val Asp His His His His His His
1               5

<210> SEQ ID NO 9
<211> LENGTH: 9
<212> TYPE: DNA
<213> ORGANISM: Artificial Sequence
<220> FEATURE:
<223> OTHER INFORMATION: NheI site 5' end of SEQ ID NO. 1

<400> SEQUENCE: 9 gctagcacc                                                              9

<210> SEQ ID NO 10
<211> LENGTH: 6
<212> TYPE: DNA
<213> ORGANISM: Artificial Sequence
<220> FEATURE:
<223> OTHER INFORMATION: XhoI site at 3' end of SEQ ID NO. 1

<400> SEQUENCE: 10 ctcgag                                                                 6
```